(12) United States Patent
Jadidi

(10) Patent No.: US 9,149,226 B2
(45) Date of Patent: Oct. 6, 2015

(54) METHOD OF AND APPARATUS FOR MONITORING OF MUSCLE ACTIVITY

(75) Inventor: Faramarz Jadidi, Hasselager (DK)

(73) Assignee: Sunstar Suisse SA, Etoy (CH)

( * ) Notice: Subject to any disclaimer, the term of this patent is extended or adjusted under 35 U.S.C. 154(b) by 217 days.

(21) Appl. No.: 13/447,930

(22) Filed: Apr. 16, 2012

(65) Prior Publication Data

US 2012/0203133 A1    Aug. 9, 2012

Related U.S. Application Data

(62) Division of application No. 10/552,366, filed as application No. PCT/DK2004/000223 on Mar. 31, 2004, now Pat. No. 8,160,689.

(30) Foreign Application Priority Data

Apr. 1, 2003 (DK) ................................ 2003 00500

(51) Int. Cl.
*A61B 5/04* (2006.01)
*A61B 5/00* (2006.01)
*A61B 5/0488* (2006.01)
*A61N 1/36* (2006.01)

(52) U.S. Cl.
CPC ............ *A61B 5/6814* (2013.01); *A61B 5/04015* (2013.01); *A61B 5/0488* (2013.01); *A61B 5/4557* (2013.01); *A61N 1/36014* (2013.01); *A61B 5/4519* (2013.01); *A61B 5/7257* (2013.01)

(58) Field of Classification Search
CPC .................................................... A61B 5/6814
USPC ............ 600/544–546, 26–28, 521, 509, 554, 600/548; 434/112, 236, 262, 308, 322, 323; 340/825.19; 345/157; 128/908; 607/48, 607/63; 84/454, 455, 477 R, DIG. 18
See application file for complete search history.

(56) References Cited

U.S. PATENT DOCUMENTS

| | | | |
|---|---|---|---|
| 6,270,466 B1 * | 8/2001 | Weinstein et al. ............ | 600/590 |
| 6,306,100 B1 * | 10/2001 | Prass ............................ | 600/554 |
| 8,160,689 B2 * | 4/2012 | Jadidi .......................... | 600/546 |
| 2004/0068196 A1 * | 4/2004 | Massicotte et al. .......... | 600/509 |

OTHER PUBLICATIONS

Lavigne et al, Sleep Bruxism: Validity of Clinical Research Diagnostic Criteria in a Controlled Polysomnographic Study, 1996, J Dent Res 75(1): p. 546-552.*

* cited by examiner

*Primary Examiner* — Brian Szmal
(74) *Attorney, Agent, or Firm* — Gifford, Krass, Sprinkle, Anderson & Citkowski, P.C.

(57) ABSTRACT

Apparatus for monitoring muscle activity, said apparatus comprising means for providing signals indicative of muscle activity, for example EMG-signals, means for processing of said signals in order to detect a particular activity and means for providing a feedback signal, wherein said device is designed in order to be individually adaptable in a set-up mode. The apparatus can be used for detecting and prevention of undesired activities such as bruxism, movements that are damaging or unwanted etc. The detection can be performed with great certainty since the individual parameters of the user are utilized for laying down reference values, threshold values, criteria for triggering of feedback signals, etc., which may take place at a set-up procedure.

14 Claims, 20 Drawing Sheets

505

METHOD OF AND APPARATUS FOR MONITORING OF MUSCLE ACTIVITY

CROSS-REFERENCE TO RELATED APPLICATIONS

This application is a divisional of U.S. patent application Ser. No. 10/552,366 filed Oct. 3, 2005, now U.S. Pat. No. 8,160,689, which is a 371 of PCT/DK2004/000223 filed Mar. 31, 2004, which claims priority of Danish Patent Application PA 2003 00500 filed Apr. 1, 2003.

FIELD OF THE INVENTION

The invention relates to an apparatus for monitoring muscle activity. Further, the invention relates to a method of monitoring muscle activity. Further, the invention relates to a method of setting up an apparatus according to the invention. The invention also pertains to uses of such a device and/or such a method.

BACKGROUND OF THE INVENTION

In a number of circumstances it is desirable to be able to monitor muscle activities of especially human beings, in particular with the objective of being able to detect and possibly avoid undesirable, unnecessary and/or potentially harmful muscle activities. In particular it is desirable to be able to detect such muscle activities with the objective of being able to interfere in such a manner that the undesirable activity may be limited or even brought to an end.

Examples of such situations are for example work situations where muscles are used incorrectly whereby irritation, pain or even damage may occur. This also relates to circumstances where muscles are strained during work stress and/or where person suffer from pain in the back of the head and shoulder caused by incorrect work position. Examples of this may be monotonous work (RSI—Repetitive Strain Injury; CTD—Cumulative Trauma Disorders; CTS—Carpal Tunnel Syndrome), work at a PC-station, (e.g. computer mouse overuse syndrome), office work (incorrect sitting) etc.

Also muscle activities may be concerned, which are brought about more or less consciously or even completely unaware, for example in the sleep, and which may also cause damage or unwanted effects.

As an example of such undesired muscular activities reference may be made to the affliction bruxism that in general is defined as powerful jaw movements without any real function and which takes the form of involuntary grinding movements of the teeth during strong clenching. This affliction may cause serious dental damages such as for example wearing of the teeth, damages to lips and the tongue, lose teeth, gingival pockets etc. Bruxism is often in addition also associated with pain in the back of the head and chronic headache.

Bruxism is normally divided into chronic and acute bruxism. Acute bruxism can happen to all and may often be observed in stress situations, for example at athletes in games or at persons that have to observe a deadline. Chronic bruxism is divided into nocturnal and daytime bruxism. Daytime bruxism is characterized by being a conscious clenching of upper and lower jaws and grinding of the teeth, although dominated by the latter. Since night-time bruxism is unconscious it may normally only be perceived by the surroundings (for example relations) as an unpleasant squeaky noise. The daytime bruxism may often be provoked by exposing the patient to stress. This daytime bruxism may be perceived as a bad habit. This form of the affliction may be relieved relatively easy by drawing the attention of the person to the bruxism. As regards night-time bruxism the problem is more complex since it is difficult to distinguish between bruxism events and ordinary muscle activity. It is noted, though, that bruxism typically lasts more than 2-5 seconds. This nocturnal form of the suffering is often alleviated by protecting the teeth with a splint.

U.S. Pat. No. 4,669,477 discloses an apparatus for treatment of bruxism. This apparatus is based on that the muscle activity in the jaw muscles of a patient can be sensed and compared with a threshold value that may be adjusted. If the sensed muscle activity exceeds the threshold value a stimulation signal is generated. The stimulation signal is applied to the jaw muscle by means of electrodes. In an embodiment of this apparatus the stimulation signal comprises a start region, where the intensity of the signal may be increased gradually, a stimulation region where the intensity is constant, and a termination region where the intensity of the signal decreases gradually.

It is however a problem that the apparatus uncritically triggers a stimulation when the threshold value is exceeded. It turns out that long time use of the apparatus has a preventive effect and that bruxism thus may be avoided without using the apparatus. The patient learns unconsciously that he/she must not grind the teeth. This is primarily caused by that when using the apparatus the patient is punished with small electric shocks in the form of the stimulation signal when the muscle activity exceeds the threshold value. Since a typical person that may or may not suffer from bruxism has a considerable muscle activity in the jaw region caused by dreaming, which activity may have the same level as real bruxism, a considerable number of stimulations of the jaw muscle will be triggered during normal sleep when the apparatus is used. With reference to the above-mentioned effect that the patient learns from the punishment he/she receives in the form of small electric shocks there is a considerable danger that the patient similarly is punished for the normal and natural jaw activity that takes place during sleep. This natural jaw activity may prove to be important for the dreams a person has during sleep.

From U.S. Pat. No. 6,093,158 A there is further known a system for treatment of inter alia bruxism. This document describes an apparatus that may be wholly inserted in the ear canal in the same manner as an hearing aid (ITE heraring aid) and where by means of a microphone sounds may be picked-up in the ear, which sounds may possibly stem from teeth grinding. By means of a processor it is investigated whether criteria for detection of bruxism are fulfilled where after a sound signal may be transmitted by means of a transducer as a stimulation to the user.

The criteria for detection of bruxism may be exceeding of a sound level that can be adjusted by the user. Other criteria such as the number of events pr. unit of time and the duration are generally mentioned. Besides from this the signal processing itself is not further described. The document mentions various options regarding detection, e.g. by means of sound sensors, microphones, EMG (Electromyographic) electrodes etc. and feedback options, for example with sound.

In an embodiment the apparatus may detect small changes in the structure of an ear by means of a transmitter and a receiver for example if the user begins grinding of the teeth. This embodiment has the flaw that the changes may possibly be quite normal jaw movements that may not be synonymous with teeth grinding. The apparatus may therefore perceive these muscle activities as undesired muscle contractions in the form of teeth grinding and thus activate the feedback In another embodiment the sound is measured in the ear, which sound may stem from grinding or snoring. No criteria are mentioned for how these sound signals/sources are differentiated from each other. This prior art system functions in the manner that a threshold value is adjusted and if this threshold value is exceeded the feedback will be activated. This means that if the user for example coughs, talks in his/her sleep or generates a normal sound during sleep, this will cause an exceeding of the threshold value and thus the patient will receive an undesired feedback.

Further an embodiment comprises additional sound sensors that may be placed at various locations on the face. If the microphone placed in the ear cannot detect the sound via the ear canal these sensors will be able to detect the sound that may inter alia stem from teeth grinding or snoring. Hereby the disadvantage will again arise that the sound source can be anything that uncritically will activate the feedback if the threshold value is exceeded.

In this prior art document it is also mentioned that e.g. other types of sensors may be placed in the mouth of the user. A sound source for use as feedback may also be placed on the body of the user or at the side of the bed. The feedback may possibly be activated in the form of a vibrator placed on a location on the body.

In the document it is thus mentioned that a stimulation feedback may be used but no explanation has been given as to how such a stimulation is activated and which criteria must be fulfilled besides exceeding of the threshold value. It is thus not explained which properties the stimulation should have.

As mentioned this known system will have the drawback that normal bite-activities, sounds, movements etc. during sleep may cause an activation of the feedback, since steps have not been taken to differentiate between these. Further, considerations have not been taken as regards the influence via the sensors from other external sources. It is thus also a general drawback that the apparatus will uncritically trigger a feedback when the threshold value is exceeded.

Finally it may be mentioned that in regard to such a prior art apparatus there will be a risk that the user is wakened during sleep, inter alia caused by feedback in situations that are not related to bruxism. This may have the disadvantage that the sleep rhythm is disturbed which will stress the user further, which again may worsen the bruxism of the user, since stress is an essential cause of bruxism.

It is thus an objective of the invention to provide an apparatus for and a method of monitoring of bruxism, by means of which these drawbacks are alleviated.

It is thus in particular an objective of the invention to provide such an apparatus and such a method, by means which an individual adaptation to the user may be achieved.

Further, it is an objective of the invention to provide such an apparatus and such a method by means of which considerations may be taken in regard to normal movements and/or sounds made during sleep that the user does not have to be "punished" for, i.e. meaning that no feedback signal will be emitted in such situations.

Additionally it is an objective of the invention to provide such an apparatus and such a method whereby it is seen to it that the user should not be awakened when the feedback is activated as a sound or a vibration etc.

It is even further an objective of the invention to provide such apparatuses and such methods that will reduce or even prevent the disadvantage that the sleep rhythm of the user is disturbed because of erroneously triggered feedback signals, whereby the sleep rhythm of the user as far as possible will not be disturbed.

Finally it is an objective of the invention to provide an apparatus for and a method of monitoring of muscle activities that may be used not only for monitoring with a view to detection of bruxism but also in a variety of other situations where it is desirable to be able to detect inopportune or of other reasons undesired muscle activities, whereby the attention of an individual may be brought to this by means of a feedback signal.

These and other objectives are achieved by the invention as explained in further detail in the following.

SUMMARY OF THE INVENTION

The invention relates to an apparatus for monitoring of muscle activity, said apparatus comprising means for providing signals indicative of muscle activity, for example EMG-signals, means for processing of said signals in order to detect a particular activity, means for providing a feedback signal, wherein said device is designed in order to be individually adaptable in a set-up node.

Hereby it is achieved that the apparatus in accordance with the invention can be used for detecting and prevention of undesired activities such as bruxism, movements that are damaging or unwanted etc, as the detection can be performed with great certainty since the individual parameters of the user are utilized for laying down reference values, threshold values, criteria for triggering of feedback signals etc., which may take place at a special set-up procedure.

Expediently, said apparatus may be designed with means for sensing and registering of a normally occurring muscle activity.

Hereby it is achieved that the apparatus will be aware of said normally occurring muscle activity that may be utilized as a reference value when laying down criteria for triggering of a feedback signal, whereby the danger of having an erroneous feedback can be reduced or even prevented completely.

In accordance with a particular expedient embodiment, said apparatus may be designed with means for sensing and registering of an essentially maximal muscle activity, for example a maximal jaw clenching activity.

Hereby it is achieved that that a measure is registered corresponding to the level of the muscle activity, e.g. the chewing force for the user in question, whereby this level may be taken into consideration when laying down criteria for triggering of a feedback signal. Hereby, an unseen high degree of user friendliness may be achieved.

In accordance with a further expedient embodiment, said apparatus may be designed for sensing and registering of muscle activity during one or more predefined normally occurring muscle activities, such as one or more grimaces.

Hereby it is achieved that muscle activities that may be expected to occur normally, are registered by the apparatus, which may be utilized when laying down criteria for triggering, whereby these normally occurring activities can not in them selves trigger a feedback signal.

In accordance with a further expedient embodiment, as specified in claim 5, said apparatus may comprise means for registering and storing muscle activity during a time interval.

Hereby it is achieved that the level of activity and possibly patterns of activity can be registered while the user is wearing the apparatus, for example for a relatively long period and/or for several periods of time, whereby reference values etc. can be established with a higher degree of certainty and accuracy. Thus, also criteria for triggering the feedback may be established with greater certainty and accuracy.

Advantageously, said apparatus may be designed to be individually adaptable by having means for adjusting said feedback signal.

Hereby it is achieved that that the individual user may adjust and set the feedback signal, e.g. a vibration, an electric signal, or another form of stimulus to a level that will be suitable to the user, e.g. a level that will not be uncomfortable to the user but that may clearly be sensed/felt/heard etc.

In accordance with a particular expedient embodiment, said means for processing of said signals in order to detect a particular activity may comprise means for pattern recognition, e.g. using FFT (Fast Fourier Transform) analysis.

Hereby an even higher degree of certainty is achieved when detecting undesired muscle activities since patterns of activity registered in advance can be utilized for establishing criteria for triggering of feedback.

Expediently, said means for providing signals indicative of muscle activity may comprise one or more electrodes for sensing of EMG-signals.

Hereby it is achieved that said muscle activities can be sensed and registered in a certain and advantageous manner.

Advantageously, said means for providing signals indicative of muscle activity may comprise one or more electrodes for sensing of EEG-signals (Electroneurographic signals).

Hereby a further increased certainty may be achieved when a feedback signal is triggered since said EEG signals can provide further information for establishing of criteria for triggering. For example when bruxism is concerned where it is known that bruxism in most cases occurs in certain phases of sleep that may be detected by means of EEG signals.

In accordance with a further advantageous embodiment, said apparatus may comprise means for testing of said electrodes and in particular the connectivity to the user by supplying a test voltage to the electrode(s), possibly as a superimposed voltage, measuring of a resulting signal and comparing the resulting current with reference value(s).

Hereby it can be assured that e.g. the user has placed the electrodes in such a manner that the resistance to the skin is below a certain value that allows the apparatus to perform without flaws. In this manner the user may initially be confirmed that the apparatus is operational when the user has placed the apparatus e.g. on the forehead and further, the electrode connectivity may be monitored periodically or continuously whereby it is detected if the connectivity falls below the prescribed range, in which case the user may be alerted and/or the operation of the apparatus may be stopped, possibly temporarily.

Preferably, said means for providing signals indicative of muscle activity may comprise a microphone, a sensor for sensing of vibrations and/or other sensor means.

Hereby it is achieved that that signals may be registered in various manners that may be adapted to the particular purpose and that further combinations of such means may be used.

In accordance with a further advantageous embodiment, said apparatus may comprise means for storing data corresponding to measured and/or processed signals.

Hereby it is achieved that data corresponding to a number of sessions, e.g. nights, may be preserved and used for e.g. statistical purposes and for assessing the improvement of e.g. user behaviour, bruxism events etc. and possibly for redefining the settings of the apparatus, for example when the user returns to a supervisor or the like.

Preferably, the apparatus may comprise means for transferring stored data to a computer, e.g. a PC or the like, which may take place at a supervisor or at the user's own PC.

Further, such data may be sent via the Internet to e.g. a supervisor for evaluation and use.

In accordance with a still further advantageous embodiment, said apparatus may be operated in a set-up mode and a use-mode, that in said set-up mode individual reference signals, signals corresponding to specific individual muscle activities and individual bio-feedback signal characteristics may be set-up, and that in said user mode the device may monitor muscle activity and provide bio-feedback in accordance with predefined rules and settings.

Hereby, the settings of the apparatus may be established in an advantageous manner. For example may the setting up be performed under supervision of a skilled and trained person, e.g. a supervisor, a dentist or the like that may lead the potential user through the procedure and may assure that the setup is performed successfully. After the setup procedure has been performed, the supervisor may put the apparatus in the use-mode, whereby the apparatus may be operated safely and in an uncomplicated manner by the user.

According to a preferable embodiment said apparatus may comprise a user module for wearing on the head, e.g. on the forehead, on or in the ear, etc.

Hereby it is achieved that that apparatus may be designed conveniently, e.g. with electrodes that may readily monitor e.g. the muscle Temporalis, and in such a manner that the apparatus may be located unobtrusively, which will be preferable if the apparatus is to be worn during sleep.

According to a further advantageous embodiment, said device may comprise a slave module and a master module, said slave module being designed for wearing by a human being.

Hereby it is achieved that the part that has to be worn by the user may be miniaturized as much as possible since components for e.g. signal processing etc. may be placed in the master module.

Preferably, said apparatus may comprise charging means, e.g. for said user module or for said slave module.

According to a particularly advantageous embodiment, said apparatus may comprise means for indicating operating steps to a user such as visual means, e.g. a LED, or acoustic means.

Hereby the user may in an expedient manner receive instructions regarding the apparatus, e.g. regarding the on/off status, regarding the level of the feedback when this is adjusted etc. Further it is noted that when the apparatus is worn on the head, e.g. on the forehead, a light indicator in the form of e.g. a two- or three colour LED may be particular advantageous since the user may be aware of the light, colour, frequency etc even when the apparatus is worn and even at night.

According to further advantageous embodiment, said apparatus may comprise display means for displaying instructions and/or results stemming from a monitoring session and/or a number of sessions.

Such display means may preferably by use of words, icons etc. indicate to the user the status of the apparatus, the operational possibilities etc. as well as further information such as statistical data concerning lapsed sessions etc. The user may for example view the display using a mirror when the apparatus is worn on the head. In this case the information shown on the display may be a mirror image, i.e. laterally reserved for the user's convenience.

The invention also relates to a method of monitoring muscle activity, said method comprising the steps of providing signals indicative of muscle activity, for example EMG-signals, processing of said signals in order to detect a particular activity, said processing of said signals taking into consideration specific individual parameters and/or references, and providing a feedback signal in case a particular activity has been detected.

Hereby it is achieved that the method in accordance with the invention can be used for detecting and prevention of undesired activities such as bruxism, movements that are damaging or unwanted etc, as the detection can be performed with great certainty since the individual parameters of the user are utilized for laying down reference values, threshold values, criteria for triggering of feedback signals etc., which may take place at a special set-up procedure Preferably, said feedback is provided on the basis of an evaluation comprising a maximum force calculation, an area calculation and/or a pattern recognition process on the basis of a FFT-processing (Fast Fourier Transform).

Further, the invention also pertains to a method of setting up an apparatus, whereby an essentially maximal muscle activity such as a maximal jaw clenching is performed and the corresponding muscle activity is sensed and registered, one or more predefined muscle activities is/are performed, e.g. grimaces, and the corresponding muscle activity is sensed and registered, and a threshold value for outputting of a feedback-signal is adjusted.

Hereby it is achieved that the expected maximal level of activity as well as normally occurring muscle activities may be registered by the apparatus, which may be utilized for establishing criteria for releasing a feedback to the user in such a manner that the criteria is adapted to the user and in such a manner that the normally occurring activities cannot trigger a feedback.

Further, the invention relates to a method of setting up an apparatus, possibly subsequent to a setting-up procedure, whereby said method comprises the steps of using the apparatus in a set-up mode, whereby values and/or parameters corresponding to individual muscle activities are registered and possibly stored for one or more periods of time, and whereby said registered and/or stored values and/or parameters are utilized for providing individual reference values for normal use of the apparatus.

Hereby the settings of the apparatus, e.g. the criteria for triggering a feedback, may be fine-tuned and adapted to a higher degree to the particular user.

The invention also relates to use of an apparatus for preventive treatment of bruxism.

Further, the invention relates to use of an apparatus for corrective monitoring of human body positioning and/or movements.

Finally, the invention relates to use of an apparatus for adjusting of human body positioning and/or movements during work activity.

BRIEF DESCRIPTION OF THE DRAWINGS

The invention will be described in further detail below with reference to the drawings of which

DETAILED DESCRIPTION OF THE INVENTION

In the following the invention will be explained in further detail with reference to a number of embodiments, of which several pertain to bruxism. It will however be understood that the invention may be utilized within a large field of applications as also stated in other places herein.

Figure 1:
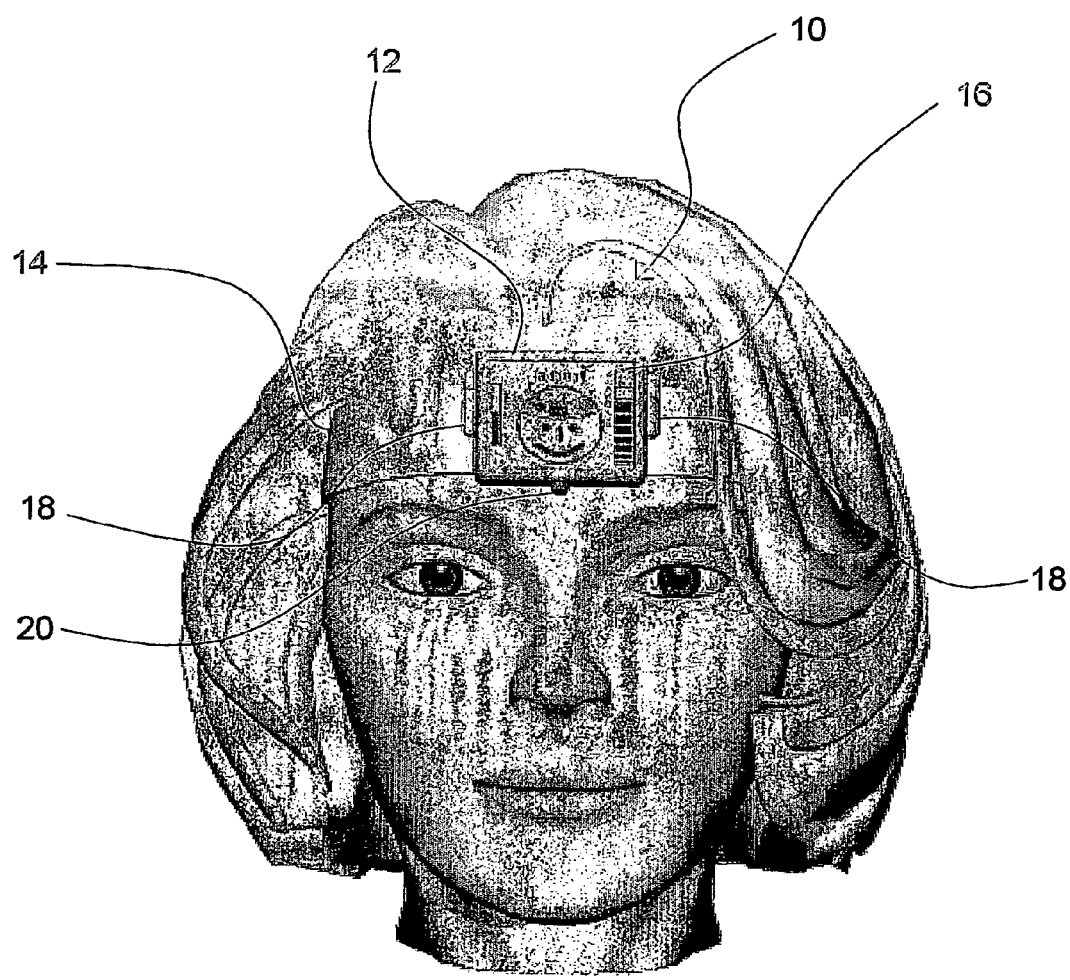
FIG. 1 shows an apparatus in accordance with an embodiment of the invention, worn by a user.

FIG. 1 shows an apparatus 10 according to a preferred embodiment of the invention for detecting and treating bruxism, e.g. for monitoring muscle activity and for providing feedback. As illustrated the apparatus 10 is worn by a user, e.g. placed on the head with a housing 12 of the apparatus placed at the forehead and a strap 14 or the like placed around the head. The apparatus comprises display means 16, a number of buttons 18, e.g. two as shown, for operating the apparatus and an indicator 20 such as an indication light, a LED or the like. The LED indicator 20 preferably comprises a three-colour LED. It will be understood, however, that more than one indicator 20 may be provided, e.g. two or more LED's etc. The functions of these means and the apparatus will be explained in detail in the following.

Figure 2:
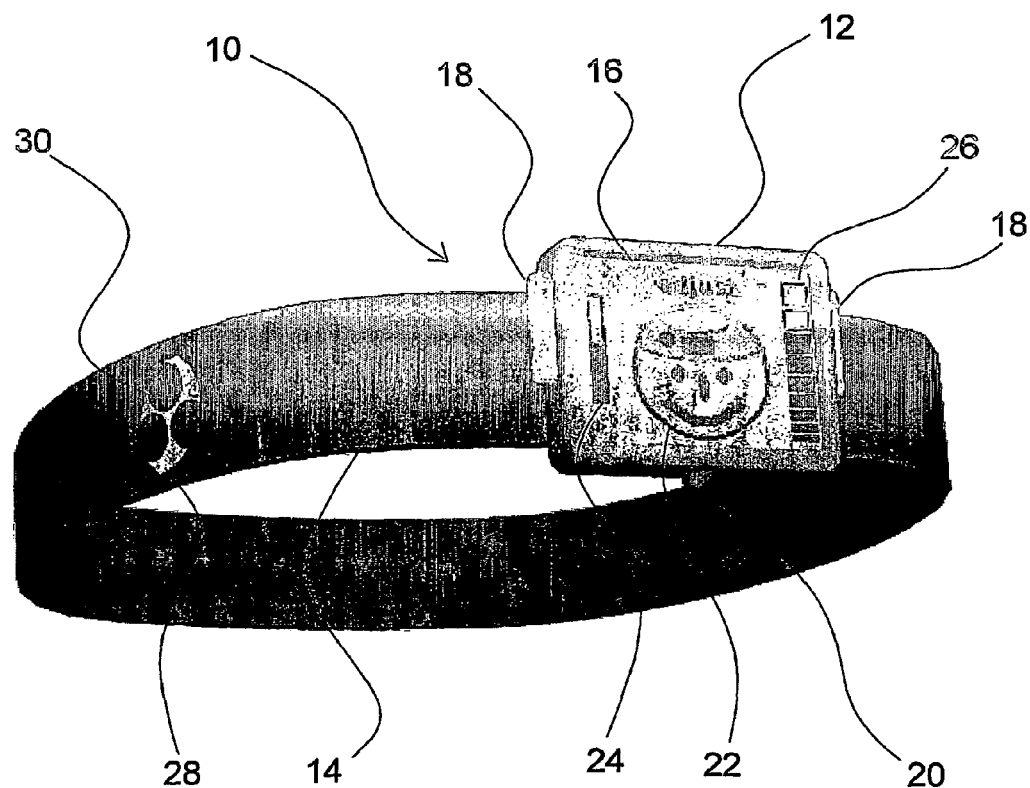
FIG. 2 shows such an apparatus in an enlarged view.

FIG. 2 shows such an apparatus in an enlarged view. It will be understood that the housing 12 of the apparatus 10 in addition to the aforementioned display means 16 etc. may contain other parts such as electronic circuitry for processing of signals etc. a microprocessor, storage means, a battery for supplying energy, etc. As indicated the display means 16 may comprise a number of indicator means and features, e.g. a battery indicator 24, an electrode connection indicator 26 for indicating the level of connectivity between electrodes and the skin of the user, and a main display 22 that may be utilized for a number of functions, which will be explained later on.

Further, FIG. 2 shows that the strap 14 may be equipped with an electrode carrier 28 comprising a number of electrodes 30 for monitoring EMG-signals (Electromyography) and/or for providing bio-feedback-signals, e.g. multi-electrodes.

As regards EMG-signals, focus will be placed on the chewing muscles when bruxism is involved. In technical language, these muscles are called muscle Temporalis and muscle Masseter, which can be utilised for the registration of EMG signals in connection with bruxism.

The Masseter muscle consists of two parts, a surface muscle and a deeper-lying part which, while strongly clenching the teeth, can easily be localised by pressing a finger into the cheek and leading it out from the mouth towards the ear. The main task of the Masseter muscle is to raise the lower jaw, although it also plays a part in the lower jaw's horizontal movement (as a part of the chewing movement). It contributes towards drawing the lower jaw forwards. Muscle Temporalis is a large fan-shaped muscle which covers and adheres to a large part of the side of the cranium, which means that most of it is freely accessible.

As mentioned, the muscle activity or the bio-activity is measured by means of electrodes, EMG electrodes, placed on the skin over the respective muscles, but other methods can also be used, such as measurement by means of sound via contact microphones etc.

In connection with the apparatus shown in FIGS. 1 and 2, the electrodes 30 may monitor EMG-signals from the muscle Temporalis. In FIG. 2 only one group of electrodes are shown, but evidently another group may be situated at the other side of the housing 12 and/or more than one group may be placed at each side of the housing 12. The electrodes are connected to the circuitry in the housing 12 by means of wires (not shown) that may be in the form of flexible wires, printed wires etc., and possibly integrated with the strap 14 or designed as an independent part situated e.g. behind the strap. The strap 14 itself may be designed in various manners, e.g. using flexible material etc. and as a part that may be adjusted, removed etc. Further, the apparatus may comprise connection means (not shown in FIG. 2) for a battery charger and/or a data connection for a PC such as a USB-connector placed in the housing 12.

According to an important embodiment of the invention, an individual adjustment to the individual user will be effected, which will be explained in the following.

Such an individual adjustment may be carried out by making use of an introductory set-up procedure, after which use may be effected through a set-up period. Hereafter, the apparatus according to an embodiment of the invention is adjusted to the user, so that the apparatus can be taken into normal use. However, the apparatus may be taken into use directly after the set-up procedure.

Figure 3:
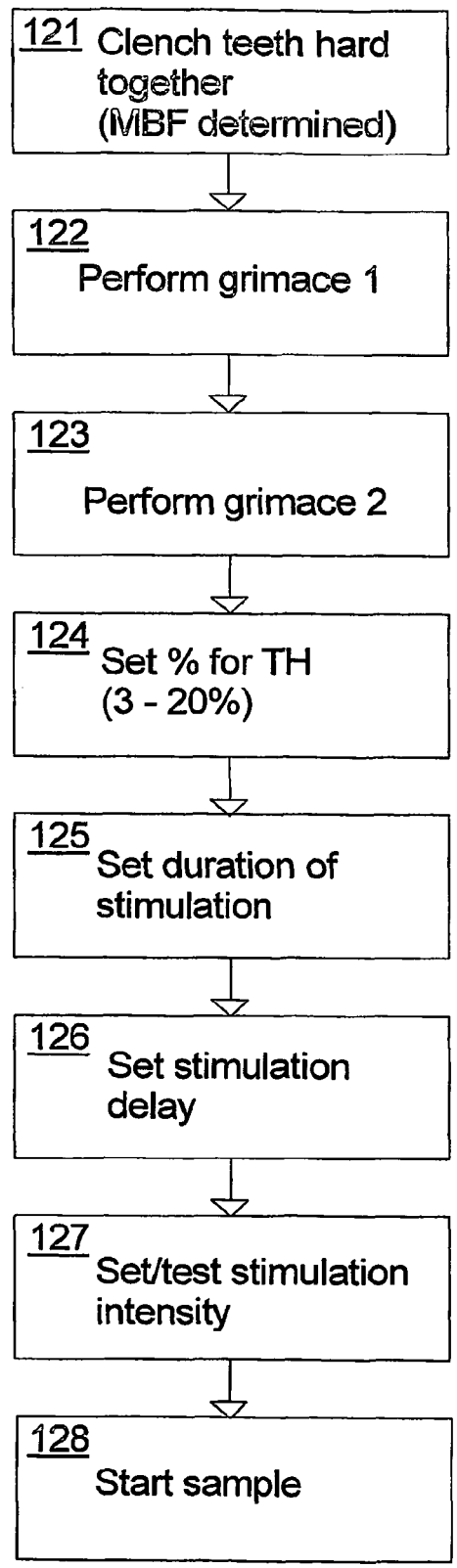
FIG. 3 shows a flow diagram for a set-up procedure according to a general embodiment of the invention.

Before describing the apparatus shown in FIGS. 1 and 2 in further detail, a typical sequence for a set-up procedure in general in accordance with the invention will be described in the following with reference to FIG. 3, which shows a flow diagram for a set-up procedure.

If use is made of electrodes, such electrodes are first mounted, e.g. either on Masseter or Temporalis muscles.

Hereafter, a strong muscle activity is measured at 121. The teeth are clenched hard together for a period of for example 10 seconds, whereby MBF (=the maximum biting force) is determined. Measurement is then made of a normally-occurring muscle activity. This is effected by two ordinary "grimaces" being made. The grimaces are made naturally without exaggerated effort for e.g. 2 seconds. A first grimace is measured at 122 and a second grimace is made for e.g. 2 seconds and measured at 123.

Hereafter, at 124 the user can key-in the desired percentage of the maximum MBF, for example in the interval of 3-20%.

On the basis of the maximum biting force and maximum grimace (the muscle activity measured at one grimace), calculation is made of a threshold value, a TH-value, which can vary from 3 to 20% of MBF.

Minimum TH-value will always be greater than the maximum amplitude of the grimaces, i.e., if for example MBF=100 and the maximum amplitude of the grimaces=10, the TH-value will be able to be selected from 11 to 20% of MBF. In this way, normal jaw movements will not have any influence on the detection of bruxism.

Hereafter, at 125 the user can select the duration of the stimulation pulse. A selection from e.g. 0.1 to 0.9 seconds may be made. The desired stimulation duration, which is used for setting the stimulation intensity, can be keyed-in so that this does not feel unpleasant for the patient.

At 126 the stimulation delay can be set. The stimulation delay is the time for which the apparatus measures the grinding of the teeth before the arrival of the stimulation pulse. Selection can be made from e.g. 0.5 to 5.0 seconds. The desired stimulation delay is keyed-in (timer definition, which will increase the certainty in connection with the detection of bruxism).

Hereafter, the intensity of the stimulation can be tested at 127 before use is made of the apparatus. All the personal parameters have now been found and the apparatus will be ready for use and/or data sampling as shown at 128.

An accumulation of data over a suitable period of time may constitute a set-up period for the apparatus, where a collection of data is provided which is specific for the user, and which may consequently be used in the determination of whether or not a feedback is triggered, for example with bruxism. Such a set-up period will be described in more detail later.

The apparatus shown in FIGS. 1 and 2 will now be described in further detail with reference to FIGS. 4 to 7 showing the display means 16 in different situations and steps of use and/or setup procedures.

Figure 4:
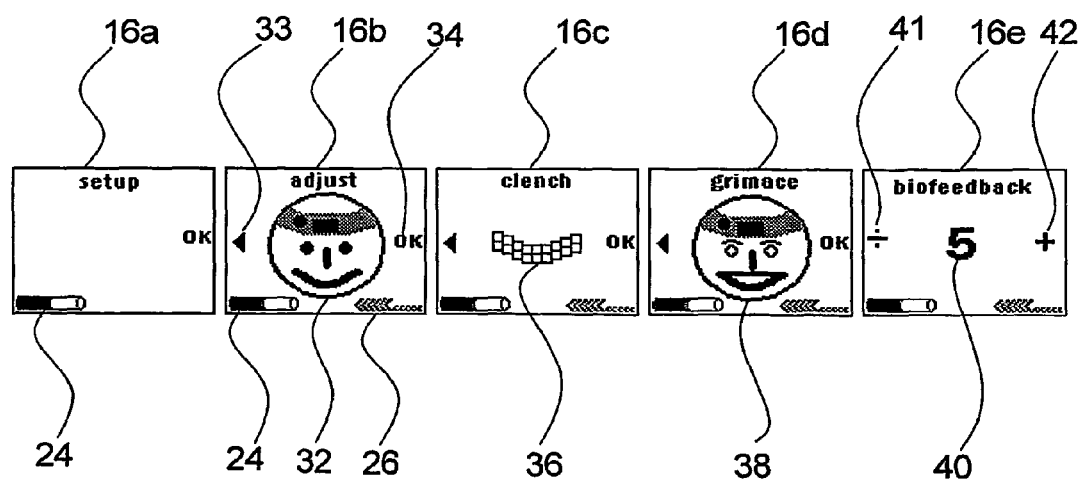
FIGS. 4 to 7 show different display images of an apparatus according to an embodiment of the invention.

FIG. 4 shows a sequence 16a to 16e of the display means during a set-up or learning procedure, e.g. where the user is introduced to the apparatus by a supervisor, e.g. a dentist, at a hospital etc.

First, the apparatus is turned on, e.g. by manipulating one of the buttons 18. The apparatus indicates that it is turned on by means of the indicator 20, e.g. LED green, and/or by means of the display means 26. It will be understood that the indicator 20 and the display 16 may show the same information simultaneously, e.g. instructions to the user. The user may view the information on the display 16 in a mirror, e.g. when the apparatus is worn on the head, but the skilled user may be provided with the same information when observing the light form the e.g. LED-indicator. As mentioned above the LED may be a three-colour LED, and the combinations of colours and/or the use of different blink frequencies may define specific information. Thus, the skilled user will also be able to operate the apparatus during the night, if needed, e.g. for adjusting the feedback level.

The apparatus is connected to a PC by means of e.g. a USB connection, and by means of a set-up software application the apparatus is put into a set-up mode by the supervisor.

The display means 16 shows the picture 16a in FIG. 4 when ready for set-up. In this picture the battery indicator 24 is also shown, which will be part of the other display pictures as well. Automatically or by operating one of the keys 18 the display means will shift to the picture 16b, indicating that the user can now put the apparatus on, after the connection to the PC has been removed, and possibly after having applied a contact gel to the electrodes 30, in such a manner that the electrodes 30 are located in close proximity to the skin at the muscles located at the temple, e.g. Muscle Temporalis. The apparatus 10 will monitor the connectivity of the electrodes to the user, e.g. by outputting a weak current on one (or more) of the electrodes 30 and by measuring the resulting difference in voltage. The result of this, e.g. the resistance between electrode(s) and skin, will be shown on the connectivity indicator 26. If the result is insufficient, the user may adjust the apparatus, e.g. adjust the strap 14, the electrode carrier 28 and/or the electrodes 30 in order to achieve a sufficient connectivity.

When it is registered that the connectivity is adequate, the apparatus automatically shifts to the next display picture 16c, showing a main display icon 36 instructing the user to clench the teeth firmly together for a predefined short period of time, and the result, e.g. the amplitude and frequency of the EMG-signals are registered. As shown in FIG. 4 at the display 16b, the two buttons 18 may have special functions in these situations, e.g. in dependence on the display picture, as shown with the symbols 33 and 34, e.g. return to the previous picture by 33 or acknowledge that the instruction has been followed 34. Similar will apply for the other display pictures in FIGS. 4, 5, 6 and 7.

Subsequent to the clenching step, the apparatus may automatically shift to the next display picture 16d, instructing the user to perform grimaces as indicated by the icon 38. This may be done by having the supervisor instructing the user to perform a number of characteristic grimaces, e.g. in accordance with the above-mentioned software application, and the results, e.g. the amplitude and frequency of the EMG-signals are registered.

The user is now instructed to shift to the biofeedback adjustment 16e, e.g. by pressing both buttons 18 simultaneously. Here, the level of the biofeedback signals, e.g. the electric stimulation signal or signals applied to the user via one or more of the electrodes 30 when a bruxism activity has been detected, is adjusted. This is done by means of the buttons 18, e.g. by reducing the level by one of the buttons 41 and increasing the level by the other button 42. As indicated, the level 40 of the feedback can be adjusted in steps, e.g. from 1 to 9. Initially, the level is set at the lowest level, and a short pulse with this level is delivered to the user. Each time the level 40 is altered, a short pulse with the selected intensity is delivered to the user. When the user has chosen an intensity level, the set-up procedure is completed, and the user may hand over the apparatus to the supervisor who by means of the PC puts the apparatus into a user-mode. The measurements and the settings are stored in the apparatus, e.g. in non-volatile storage means, whereby the settings etc. will not be influenced by battery shift and/or battery charging etc.

Figure 5:
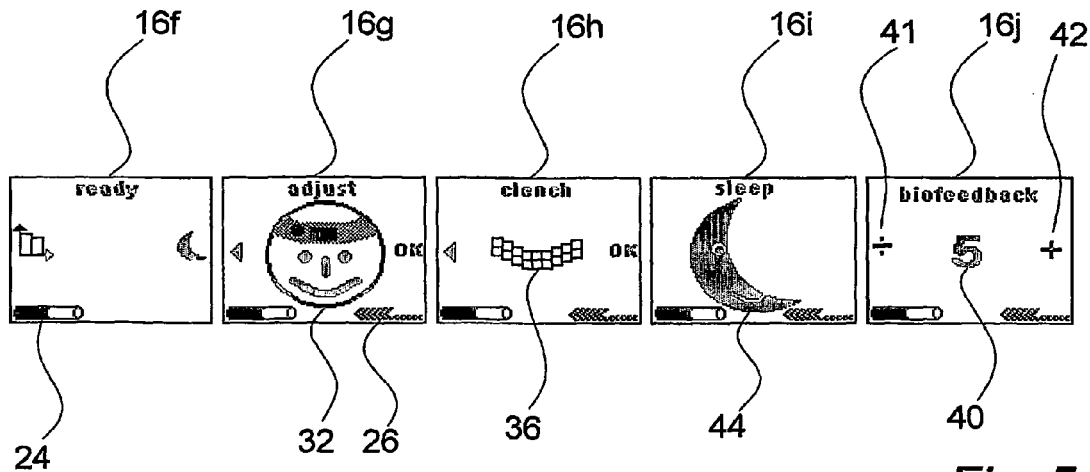

The ordinary use, i.e. use of the apparatus in the user-mode is illustrated in FIG. 5. As previously described for the set-up procedure the apparatus is activated, i.e. turned on by operating one of the buttons 18, whereby the display means will show the "ready"-picture 16f, including the battery indicator 24. Contact gel can be applied at this stage or before activating the apparatus. The apparatus will automatically—or after having manipulated a button 18 again—shift into the "adjust"-picture 16g showing the "adjust"-icon 32. The user puts on the apparatus 10 and adjusts the strap 14 until the electrodes 30 are in close proximity to the skin and placed at the location of the muscle Temporalis. As described above, the apparatus monitors the connectivity of the electrodes 30 and when the result is found to be adequate (which is also shown on the connectivity indicator 26), the apparatus shifts automatically into the next display image 16h, whereby the user is instructed by the "clench"-icon 36 to clench the teeth hard together for a short moment. The apparatus measures the amplitude and frequency of the EMG-signal and shifts automatically to the next display picture 16i that by means of the icon 44 indicates to the user that he/she may now go to sleep.

In a modified embodiment of the invention it may not be necessary to perform a measuring of the clenching in the use-mode, e.g. the apparatus will be able to perform automatically. Thus the step relating to the measuring of the clenching, e.g. related to the display image 16h, will not form part of the procedure in the use-mode environment, but only during the supervised set-up procedure.

For both of these embodiments the apparatus will hereafter monitor the user on the basis of the EMG-signals from the user and if a bruxism activity is detected on the basis of the settings and parameters already registered, a biofeedback signal is delivered to the user. In this mode the display 16 will be turned off after a predetermined time of inactivity, i.e. a period of time, in which the buttons have not been manipulated. However, the user may at any time, e.g. during the night, adjust the biofeedback level by operating both buttons 18 simultaneously as previously described, whereby the display image 16j will emerge and the intensity level may be reduced (41) or increased (42).

Figure 6:
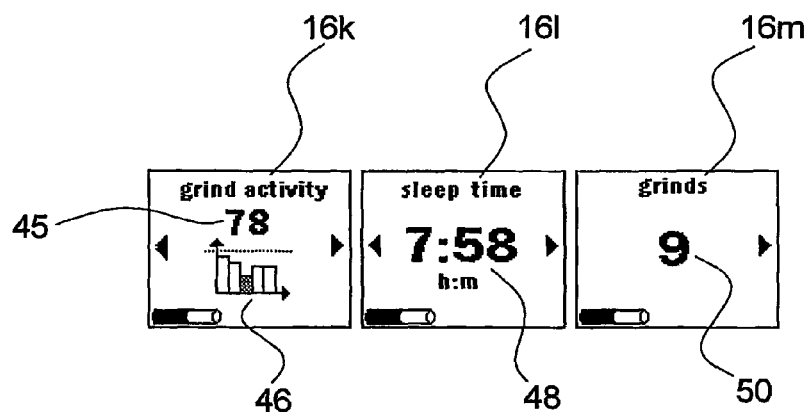

When the user wakes up again, e.g. next morning, and takes the apparatus off, the display means will be turned on again automatically, and the user may now use the two buttons 18 to display information regarding the lapsed sleep session and information regarding the lapsed session in relation to earlier sessions, e.g. in order to illustrate any development. This is shown in FIG. 6, where the first display image 16k shows a number indicated by 45, e.g. a "magic" number or a performance number which indicates an overall grind (or bruxis) activity. This number may be calculated on the basis of the number of grind or bruxism activities or events during the night (or session), the accumulated or total grind time, the intensity of each of the grind events etc. in relation to the lapsed time during the session and on the basis of an algorithm or the like. The overall grind activity may thus be illustrated by a "magic" number or a performance number between 0 and 99, where the number 0 is designated as the lowest grind activity. Further, in this display image a graphic overview 46 of the grind activities or events during the preceding sessions or nights, for example the preceding 7 nights are shown, for example in the form of a bar graph 46. In this manner the user may immediately review the development, e.g. improvement in the grind activity. If for some reason the information related to a session cannot be used, e.g. if the electrode connectivity has been below the required level or if the battery level has been inadequate, the bar in question may be shown with e.g. a different colour or pattern to indicate that this particular bar should be omitted when assessing the result.

The next display image 16l shows the total lapsed time 48 during a session, e.g. a night's sleep. The last display image

16m in FIG. 6 shows the number 50 of occasions during a session that a grind or bruxism activity has been detected.

Figure 7:
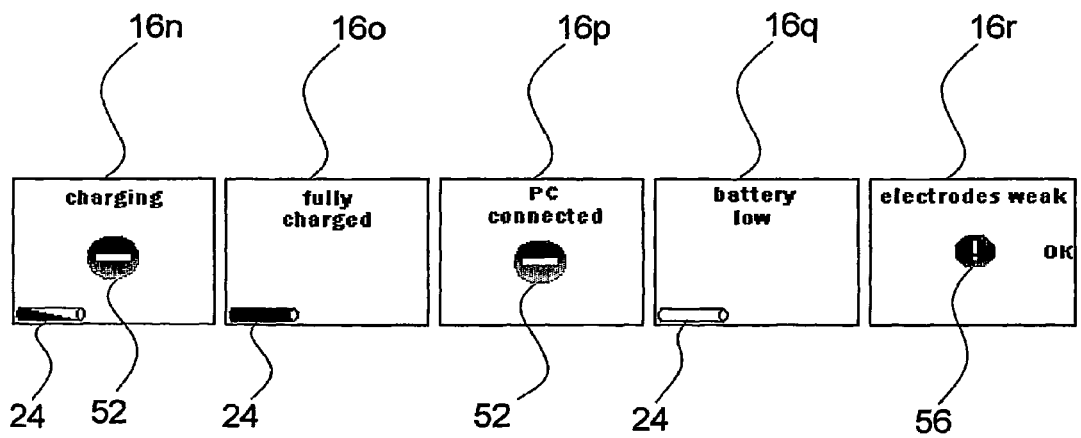

In FIG. 7 a number of further display images are shown. The display image 16n shows that the battery in the apparatus is being charged as also indicated by the battery indicator 24. Further, the icon 52 indicates to the user that the apparatus cannot be used. The image display 16o indicates to the user that the battery now is fully charged and that the charge connection may be removed. The image display 16p indicates that the apparatus is connected to a PC, e.g. for transferring of accumulated measured and registered data to the PC for processing and/or transmission to a supervisor, a dentist etc., and that the apparatus cannot be used as indicated by the icon 52. Further, the image displays 16q and 16r shows two fault situations that might arise and render the data stemming from a session unsuitable for statistical use etc. The image display shown as 16q indicates that the battery has not sufficient charge capacity left for a session, e.g. an 8 hour session. The last of the image displays 16r indicates that the electrode connectivity has been below standard for a predetermined accumulated period of time, thereby rendering the results achieved during a session unsuitable for further processing, statistical use, etc.

In this connection it is noted that information to the user shown on the display, e.g. warnings regarding battery charge, electrode connectivity etc. is also provided to the user by means of the indicator 20. This may take place by having the indicator 20 take different colours, e.g. three different colours and combinations hereof, and by having the indicator be lit continuously or blink with different blink frequencies.

Figure 8:
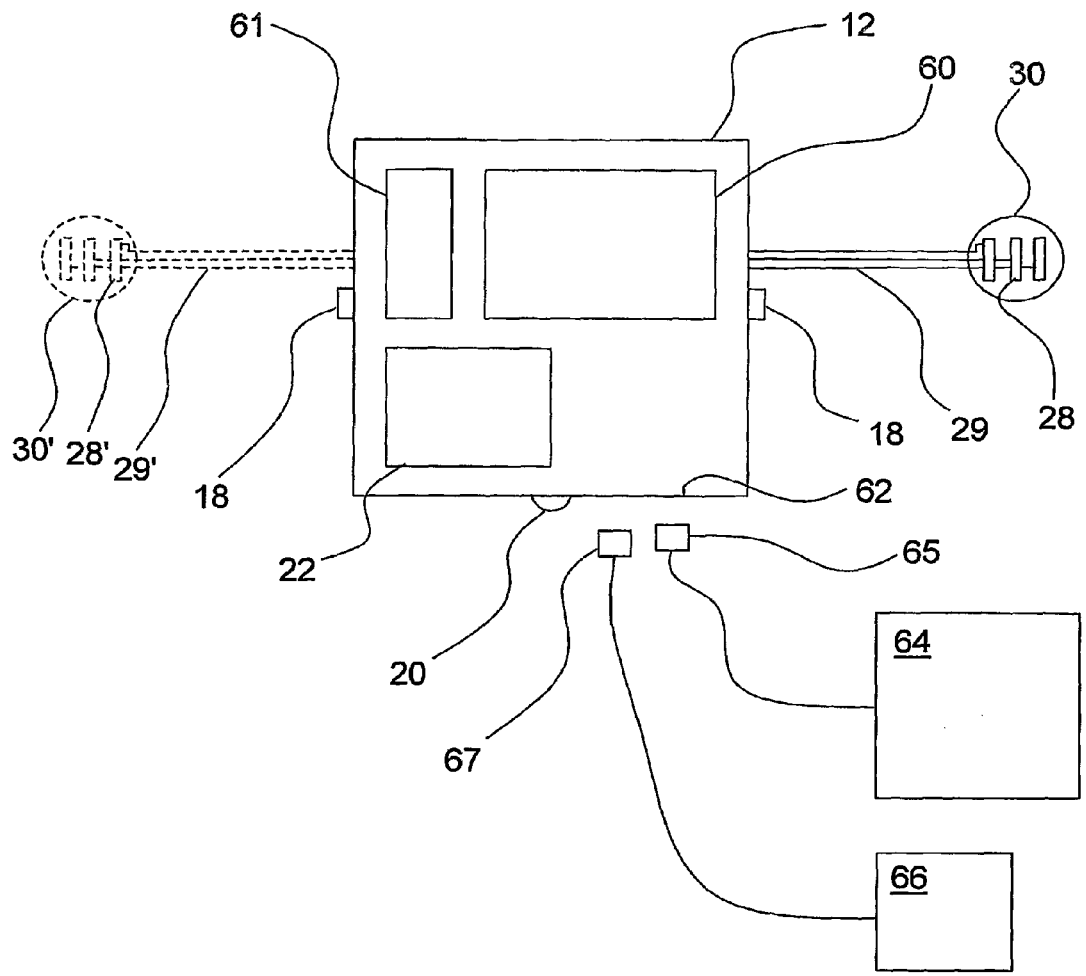
FIG. 8 shows in block diagram form a general overview of an apparatus as illustrated in FIGS. 1 and 2.

In FIG. 8 a general overview of an apparatus as described above has been shown in block diagram for, e.g. showing the main components of such an apparatus. Thus, the housing 12 is illustrated comprising a microprocessor 60 for processing signals, storing settings, data etc. and facilitating transmission of biofeedback signals etc. Further, the housing 12 comprises the main display means 22 and an energy supply source in the form of a battery 61. As already described the housing 12 has a number of buttons or keys 18, a visual indicator 20 in the form of e.g. a LED and a plug-in connector 62, e.g. a USB connector or the like. This connector 62 may be connected to a PC or the like 64 by means of a connector plug 65, e.g. for setting up the apparatus or for transmitting data to the PC, from which it may be transmitted to a supervisor, e.g. a dentist or a medically trained person. Further, the same connector 62 may facilitate a charging of the battery 61 since a plug connector 67 from a charger 66 may be connected.

Further, it is shown in FIG. 8 that an electrode assembly or carrier 30 comprising a number of electrodes 28 is connected to the apparatus by means of wires 29. This assembly may be situated to the right or to the left. In either case the monitoring will be performed on the muscle Temporalis. Additionally, a further set of electrodes 28' carried by a carrier 30' and wires 29' may be connected to the apparatus, e.g. for monitoring muscle Temporalis at the other side of the housing. In most cases a single electrode assembly will suffice, but in some cases bruxism may be located at one side only or the bruxism events may differ from one side to the other.

Figure 9:
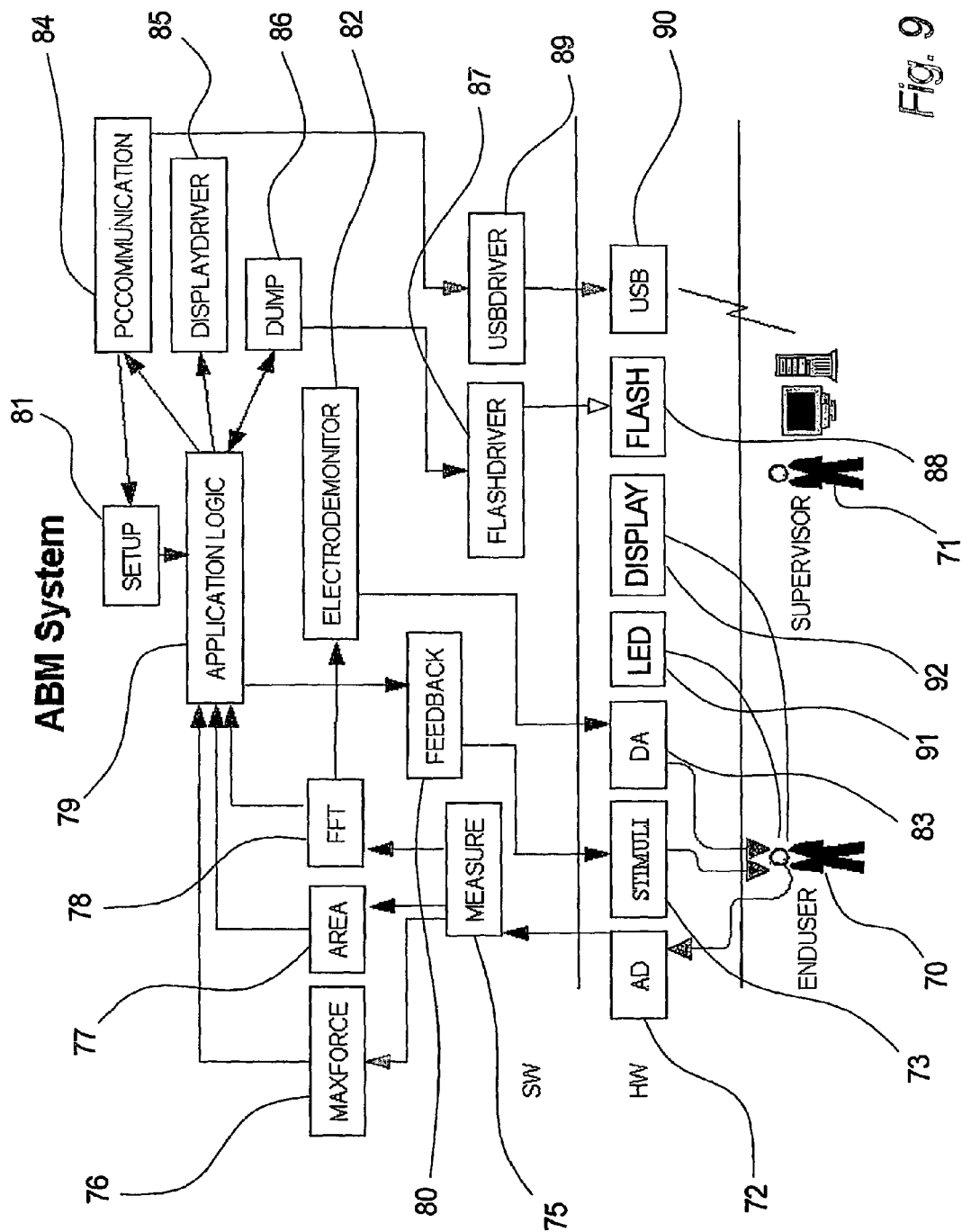
FIG. 9 illustrates a system in accordance with a further embodiment of the invention in block diagram form.

FIG. 9 illustrates a system in accordance with a further embodiment of the invention in block diagram form, e.g. an anti bruxism module system ABM system. Here an end-user 70 and a supervisor 71 are shown in the lower level. Above these there is shown the hardware level HW and in the upper half of the figure the software level SW. EMG-measurements from the end-user 70 is performed via an AD-converter 72, from which the signals are delivered to a measure block 75. The registered signals are used in three types of processing: for evaluating in accordance with a maximum force calculation 76, for evaluating in accordance with an area calculation 77 and for evaluating in accordance with a FFT-processing (Fast Fourier Transform) 78. These will be described in further detail below. The output from these three evaluations are provided to the application logic 79, where it is evaluated whether a feedback should be triggered or not in accordance with the setting that has been performed via the setup-part 81. If a feedback signal is to be delivered, this is delivered via a feedback part 80 to a stimuli interface 73 and to the end-user 70. Further FIG. 9 illustrates the electrode monitoring that is performed via a part 82 that sends a signal with a small amplitude and a predefined frequency to the end-user via a DA-converter 83. This signal is measured via the blocks 72, 75 and 78, where it is recognized by the predefined frequency, whereby the electrode monitor block 82 may evaluate the electrode connectivity. This and other information may be shown on the display 92 and/or indicated by means of the optical indicator 91, e.g. a LED indicator. It is noted that any information that is needed for operating the apparatus may be provided to the user by means of the display 92 as well as by means of the LED indicator 91 as previously described.

As also previously described the setup of the system may be performed using a PC communication 84 that also may serve to download data from the apparatus, e.g. via a USB driver 89 and a USB connection 90 to a PC at e.g. the supervisor 71. Further, a display driver 85 for operating the display 74 and/or the LED indicator 91 is shown and a block for performing a dump 86 of data via a flash-driver 87 to storage means in the form of e.g. a flash memory 88 is also shown.

Figure 10:
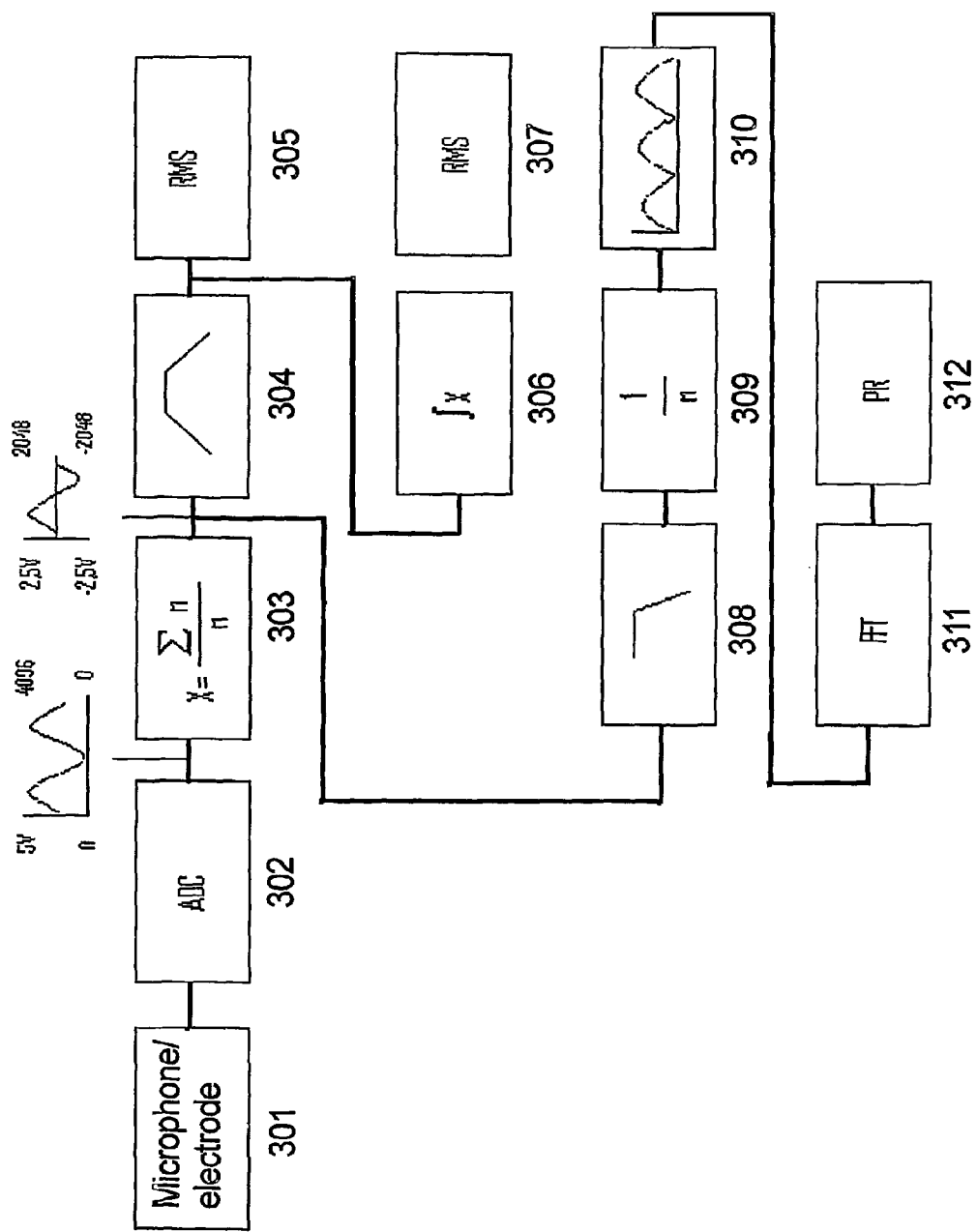
FIG. 10 shows a block diagram of a signal processing method in accordance with several embodiments of the invention.

For further exemplification of the invention and various embodiments, a block diagram in FIG. 10 shows signal processing methods according to the invention. The raw data recorded from microphones, electrodes or with other means 301 is sent to a microprocessor for a further analysis of the signal as follows:

At 302: The signal is amplified (possibly 0-5V) and is then sent to an ADC (possibly 12-bit, 5V=4096).

At 303: All DC is removed, i.e. the average value is calculated, so that the signal will lie symmetrically around the 0 point (±2.5V=±2048).

Hereafter, the following signal processings are possible, namely:

1) One can select to make an RMS calculation of the signal, where the result is compared with a predetermined table which contains reference frequencies (determined during the set-up period) from the patient's occlusion reliefs during bruxism. I.e. if a frequency pattern (or more) can be recognised from the table during the continuous accumulation of data from the patient, the feedback (stimulation) will be activated.

This takes place as shown in FIG. 10.

At 304: The signal is filtered in a band-pass filter.

At 305: The RMS value is calculated.

2) The RMS determination is effected followed by an integrator, whereby the certainty with regard to detection of bruxism will be further increased.

Otherwise the same method as described under 1) is used.

At 306: The signal is integrated.

At 307: The RMS value is calculated.

3) An even more secure method for the detection of bruxism is that of carrying out an FFT (Fast Fourier Transform) analysis of the signal, as described in the following:

When the average value of the signal is determined at 303, the signal is sent to a low-pass filter 308 where all noise and unusable signals are filtered out. Thereafter, the signal will be averaged and rectified, 309 and 310; and an FFT analysis is effected at 311 so that the frequency content of the signal is determined. In this way, which frequencies are collected in the system can be ascertained with high certainty. Thereafter, a Pattern Recognition of the signal must be carried out at 312.

Figure 11:
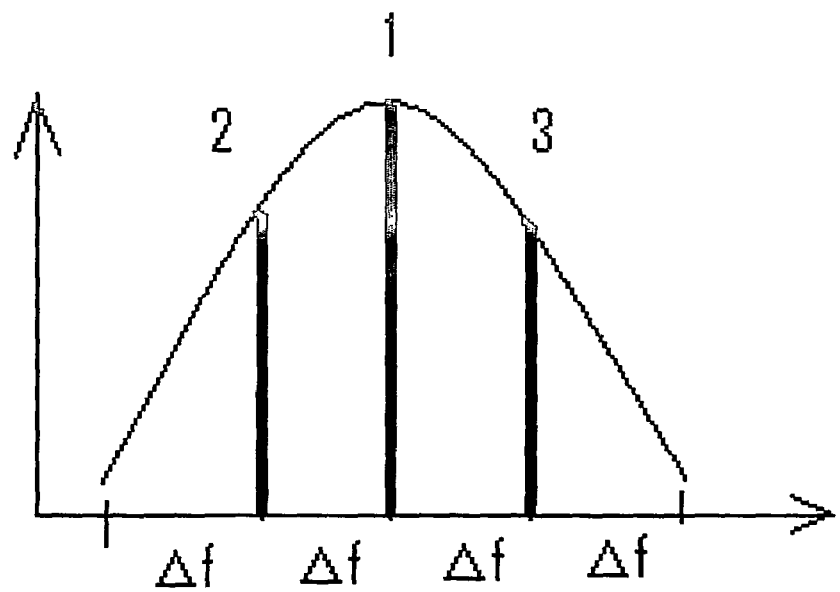
FIG. 11 illustrates Peak Detection by means of a folding principle.

The principle is that there is first carried out a so-called Peak detection, where on the basis of the FFT analysis and the folding principle the highest peak value (amplitude value) is found, such as is illustrated in FIG. 11.

This means that a folding of the signal is effected, where one can find out how the signals with the given frequency content lie in relation to one another. It is ascertained which frequencies lie closest to the frequency 1, which in this case are the frequencies 2 and 3.

The method is a stochastic signal processing where the patient must first use the apparatus for a period (approx. 7 nights) without activation of the feedback. This is an individual adjustment where it must be registered which frequency patterns are formed when the patient grinds his/her teeth (with regard to determination of the frequency patterns, reference is made to the article Lavigne G J et al (1996), J Dent Res 75(1): pp. 546-552, possible frequency patterns phasic, tonic, and mixed). When these frequency patterns are determined, they are collected in a table and stored in a memory which is accessible for the microprocessor.

With the registration of bruxism via the apparatus such as shown in FIG. 10, a correlation can be ascertained between the frequency content of the signal from the continuous measurements (recorded from the microphones/sensors, 301) and the recorded signals which lie in the table. After this registration, the following must be carried out:

One first looks at the $1^{st}$ harmonic frequency (1 in FIG. 11).

If there is a match, a look is taken at the $2^{nd}$ and $3^{rd}$ harmonic frequency (2 and 3 in FIG. 11). In order to further increase the certainty, a look can also possibly be taken at the $4^{th}$, $5^{th}$, $6^{th}$ harmonic frequencies if this is necessary. However, as a rule it is not necessary to go so high up in harmonic frequencies for detection of bruxism.

I.e. when these harmonic frequencies match the frequency content of the signals from the table (stored in the memory), it can with certainty be ascertained that the patient is grinding his/her teeth (bruxism), and the feedback may necessarily be activated.

In this manner, the certainty with regard to the detection of buxism will be very great (close to 100%), so that the patient does not get punished for normal teeth-clenching activity during sleep.

The difference between this method and all the other existing methods is that this apparatus focuses only on the detection and herewith the treatment of bruxism, where all the normal biting activites, possible external disturbances/sources etc. are eliminated.

As mentioned earlier, an accumulation of data etc. is carried out during a set-up period which will be described in more detail in the following. During this set-up period, the apparatus is set individually where, for example, the patient can use the apparatus for a min. of 7 nights in succession, without activation of the feedback. In this way, all the personal parameters related to bruxism are registered and stored in a table (personal table), which during the signal processing will be used for pattern recognition as shown at 312 in FIG. 10. The apparatus can be configured and set in such a manner that the feedback can be activated only when the threshold value is exceeded, and as a minimum the $1^{st}$ harmonic frequency, cf. FIG. 11, matches one of the frequencies which lie in the table.

According to a further embodiment of the invention, it is taken into account that the stimulation shall be able to be adjusted individually. For example, on the basis of the table it can be ascertained which feedback fits the patient's bruxism pattern, where the feedback (the stimulation) is set regarding duration, intensity and delay. This means that if the patient has a tendency to grind teeth e.g. for 3 seconds and then cease grinding for up to 1-2 minutes, and thereafter repeats this teeth-grinding pattern in this periodic manner, a stimulation with a higher intensity and shorter duration will be required in order to optimise the efficiency of the feedback. On the other hand, if the patient grinds the teeth for longer periods with shorter intervals, then use must be made of a stimulation which is ramped up with determined sequences and longer duration. I.e. in accordance with bruxism patterns determined during the set-up period, the feedback will automatically be set/adjusted so that it is most effective for the patient. This optimises the treatment of bruxism. At the same time, importance is attached to the patient not being awakened by the feedback (the stimulation).

Moreover, it should be noted that a further advantageous embodiment of the invention comprises a division of the apparatus into a master part, in which the processing of the signal itself is effected, and a slave module in which signal recording, possibly digitalisation and transmission to/from the master module is carried out. Furthermore, feedback can be effected via the slave module or it can be effected via a separate module.

With this dividing of the apparatus, where the transmission of data takes place in a chiefly wire-less manner, the weight, extent etc. of the slave module or the modules can be minimised so that the user is aware of this to a lesser degree. Moreover, the user can move relatively unhindered by the slave module.

The processing of the signal in the master module, which for example can be a microprocessor-equipped apparatus or the like placed in the vicinity of the user, for example at the side of the bed, will now be described in more detail with reference to FIG. 12.

The master module consists of main processor 610 and transmission interface 612 to a PC, and a transmission interface 611 to the slave module.

The data from the slave module is transmitted to the master module where all data/signal analysis for the handling of bruxism takes place in the main processor 610. The result of the data analysis (in cases where periods of bruxism can be ascertained) is sent back e.g. to the slave module via 611, where the bio-feedback is activated, or to a separate external module, such as a vibrator module, where bio-feedback is effected.

All the data is transmitted and stored in the main processor 610, where via 612 it is possible to send the data further to a PC.

Figure 13:
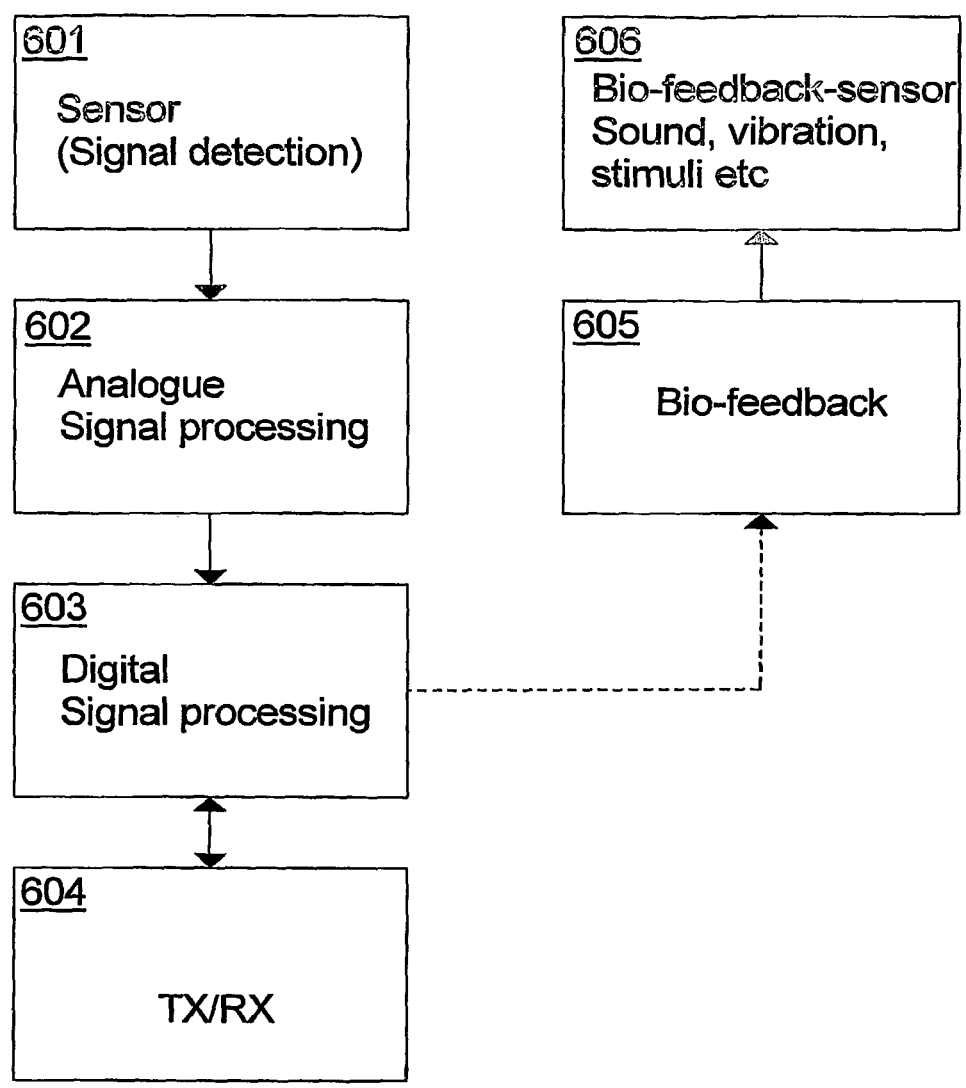
FIG. 13 illustrates signal processing in a slave module according to a further embodiment of the invention.

The processing of the signal in the slave module will now be described in more detail with reference to FIG. 13.

The signals in the form of sound, muscle movement/contraction and EMG are detected by a sensor 601 (microphone, electrode, piezo-sensor etc.). These signals will be processed in the analogue circuit 602 and are sent further to a processor 603.

The digitalised data is transmitted 604 to a stationary main processor (master module, cf. FIG. 12), where the necessary data analysis is carried out, such as disclosed in the claims and the description.

When the necessary/mentioned criteria for bruxism have been fulfilled, a signal will be sent via 604 to the processor 603, after which a bio-feedback signal 605 is activated in the form of sound, vibration and/or other stimuli, which via 606 is sent to the patient. The bio-feedback can be entered either in the slave module or into a further part such as a vibrator module, a bracelet vibrator or the like.

In the following, various other embodiments of the invention and their practical configuration will be described in more detail with reference to FIG. 14-20.

Figure 14:
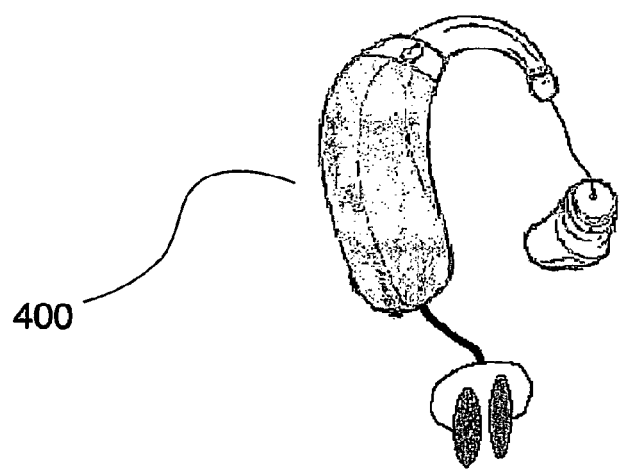
FIGS. 14-16 show a further embodiment of the invention comprising a slave module for placing at an ear.
Figure 15:
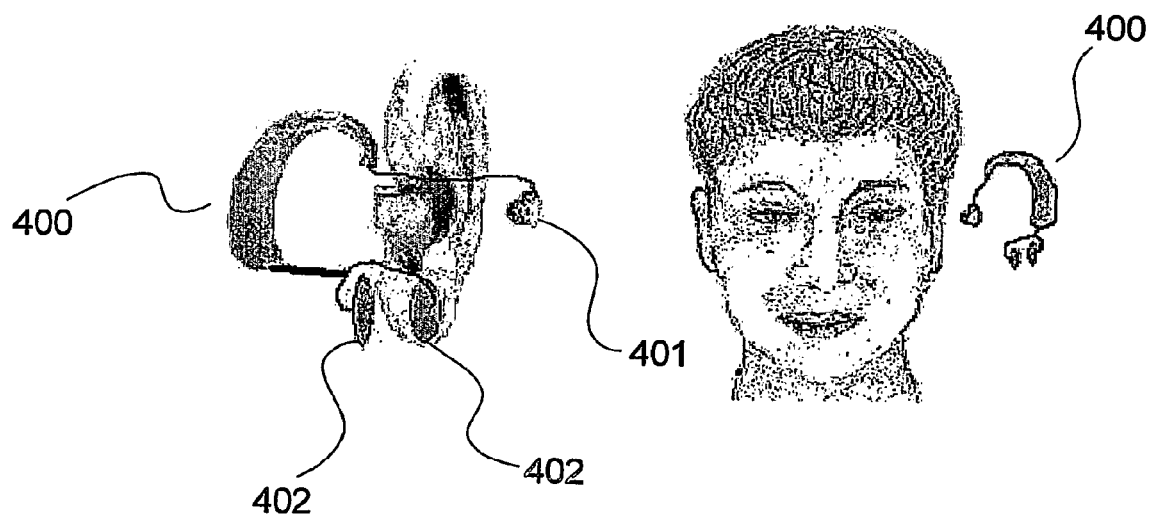
Figure 16:
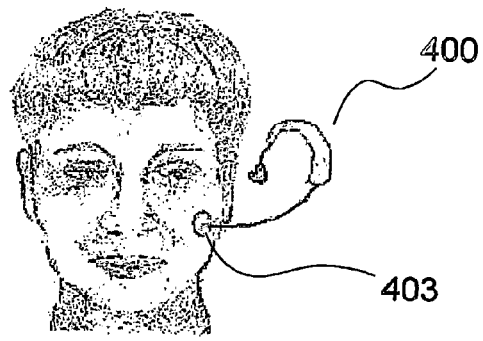

A first embodiment of a slave module according to the invention is shown in FIG. 14-16. Here, there is shown an embodiment 400 of the apparatus which can easily be placed behind the ear. FIGS. 15 and 16 illustrate how the apparatus shall be used. The signals (generated by grinding of the teeth) are detected via a microphone 401, and the feedback in the form of stimulation is connected possibly to the ears by means of the electrodes 402.

As shown in FIG. 16, the stimulation electrodes 403 can instead be placed on the masseter muscles.

Figure 17:
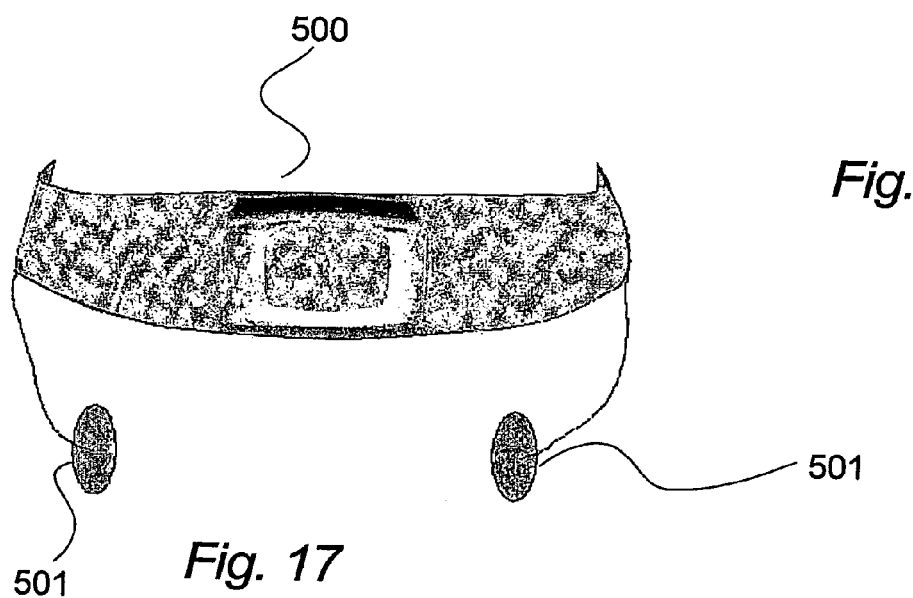
FIGS. 17-21 show an even further embodiment of the invention, also comprising a slave module.
Figure 18:
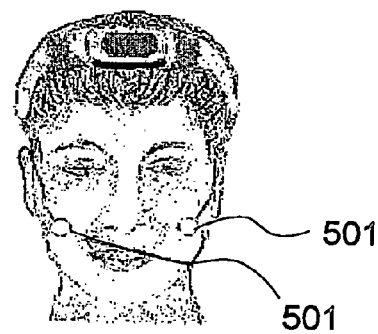

A second embodiment of a slave module is shown in FIG. 17-20. As shown in FIG. 17, this embodiment of the apparatus 500 (the slave module) is configured in such a manner that it resembles a headphone, so that it can easily be placed either on the patient's head or forehead. The apparatus is configured as a slave module which can communicate in a substantially wire-less manner with a master module. This master module can comprise the most essential parts of microprocessors, memory units etc., so that the slave module needs only to comprise a transmitter/receiver, and circuits which are necessary for the leading of signals to/from electrodes, sensors and/or transducers.

The EMG signals from the masseter muscles are detected via the electrodes 501 and processed in the slave module 500. The bio-feedback in the form of stimulation is connected to the same electrodes 501. The electrodes 501 are used for both detection and stimulation.

Figure 19:
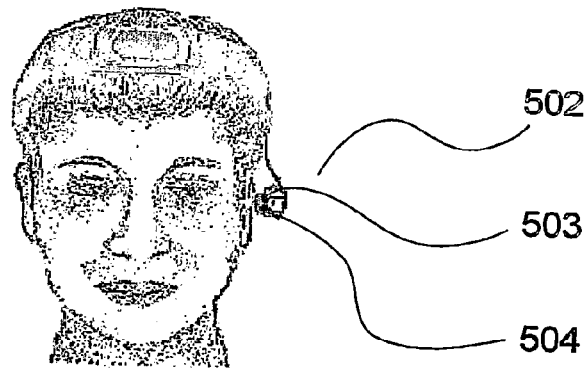

Instead of the electrodes 501, there can possibly be connected an integrated system 502 which contains both a microphone 503 and a loudspeaker 504 on the apparatus. The microphone is used for the detection of frequencies generated by bruxism, and the loudspeaker 504 is used to send the bio-feedback to the patient in the form of sound/frequency. The principle is illustrated in FIG. 19.

Figure 20:
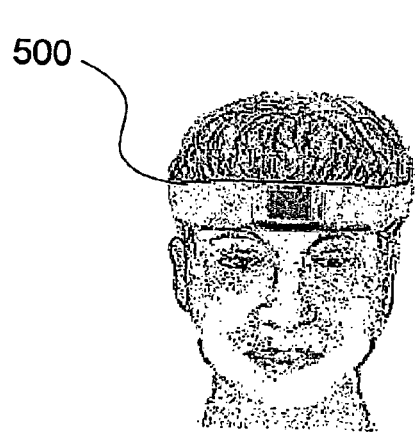
Figure 21:
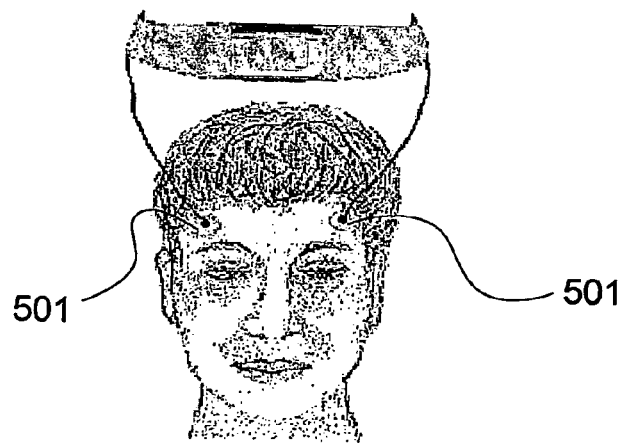
Figure 22:
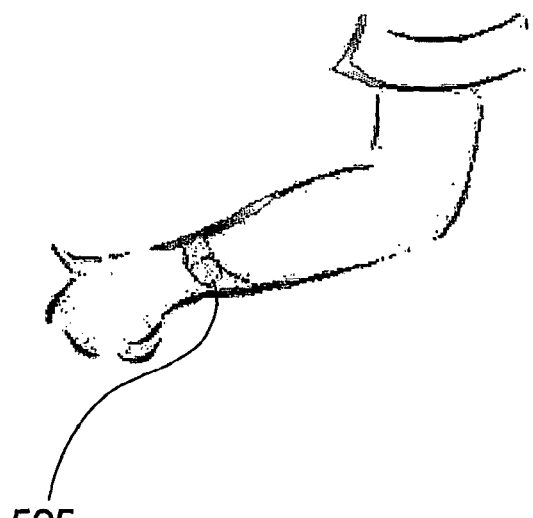
FIG. 22 shows a particular stimulation module, for example a vibrator module, according to an even further embodiment of the invention.

The electrodes for the detection of EMG activities can possibly be placed on temporalis muscles as shown in FIGS. 20 and 21, where the bio-feedback, e.g. in the form of a vibrator 505, can possibly be placed on the patient's arm in the form of a bracelet vibrator, such as illustrated in FIG. 22.

The slave module 500 and the bracelet vibrator 505 can preferably communicate in a wire-less manner (separate) with the master module.

The vibrator 505 shall only receive signals (only RX) from the master module, which is described in connection with FIG. 12, where the bio-feedback in the form of vibration is activated when bruxism is detected from the slave module 500.

Figure 12:
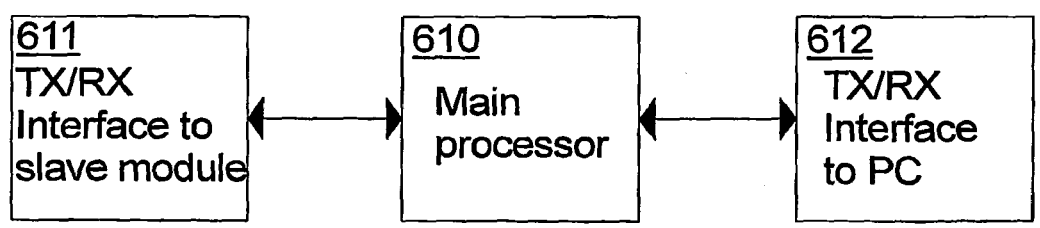
FIG. 12 illustrates signal processing performed in a master module in accordance with a further embodiment of the invention.
Figure 23:
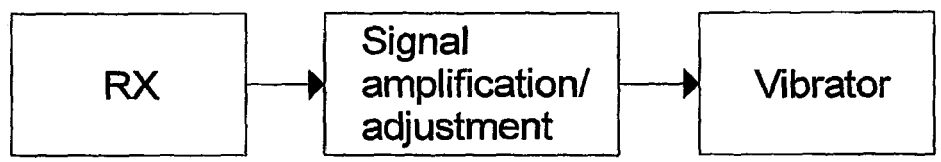
FIG. 23 illustrates the signal processing in connection with a vibrator module.

When the necessary/mentioned criteria for bruxism have been fulfilled, a signal will be sent from the master module (as shown in FIG. 12) to the vibrator 505, where a bio-feedback signal is activated in the form of vibration. The signal processing for this function appears from FIG. 23.

When, for example, the apparatus is used in the combination as shown in the FIGS. 20 and 21, the biofeedback part 605 and 606 can possibly be placed in the bracelet vibrator 505.

Figure 24:
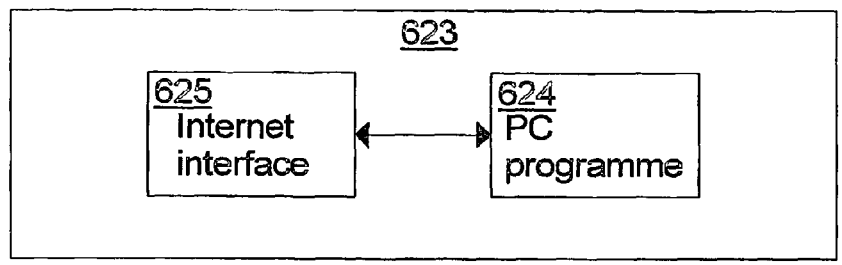
FIG. 24 illustrates the data processing system in a PC in accordance with an embodiment of the invention.

The data analysis and the processing in the PC will now be described in more detail with reference to FIG. 24.

All data which is stored in the master module can be transferred to a PC via 612 for a further analysis of the processing period. A programme 624 which can receive the data is installed on a PC 623. In the programme 624, all data from the patient (for each night) is processed systematically to determine the efficiency of the processing period. In this way the patient himself can follow the course of events. The patient can possibly send the data further to his doctor/dentist via the programme interface 625, which can establish connection to the Internet.

Figure 25:
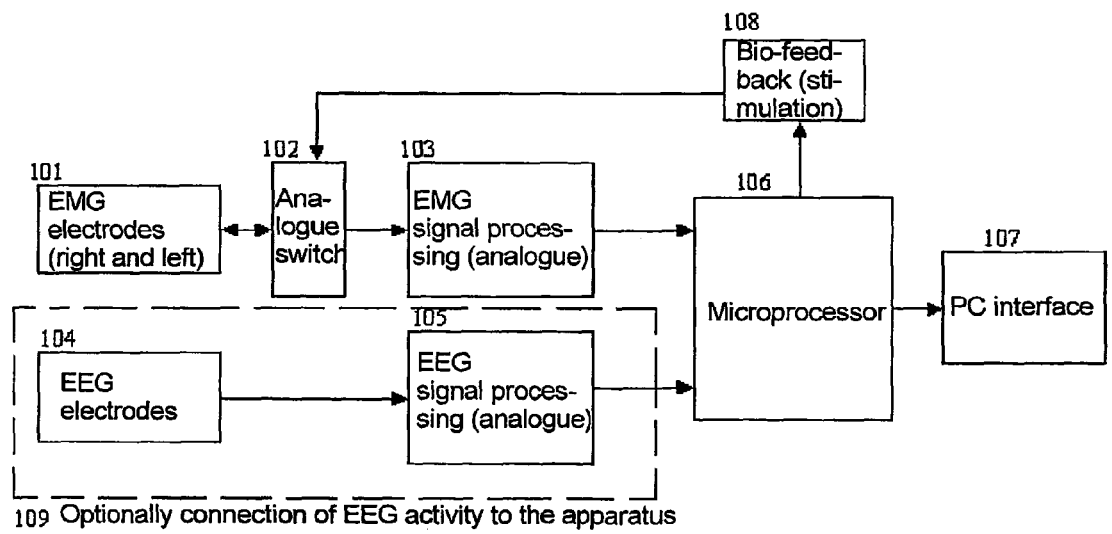
FIG. 25 shows a block diagram for a further embodiment of an apparatus according to the invention.

A still further example of an embodiment of an apparatus in practice will be explained with reference to FIG. 25, which shows such an apparatus in block-diagram form. By means of the apparatus, it is possible to stimulate the jaw muscle of people who are in the habit of grinding their teeth, so that the jaw muscle is relaxed and the disturbing teeth grinding/bruxism is avoided.

The signals from the electrodes 101 are sent via the analogue switch 102 to the EMG signal processing part 103.

In a preferred embodiment, use is made of so-called multi-electrodes which can be used both to stimulate a muscle and to register the muscle's activity. The multi-electrode's function, respectively to transmit or register signals, is controlled by an analogue switch 102 from the microprocessor 106.

Analogue signal processing is carried out in 103, where the bio-potentials recorded from the electrodes 101 are amplified, filtered and rectified, so that the processor 106 can be utilised to the best possible degree.

The signals from both electrodes 101 are sent to the microprocessor 106, where communication between the microprocessor 106 and connected circuits takes place via a bus system.

The task of the microprocessor is to carry out the signal processing of the EMG sampled by the analogue-to-digital converter and possible EEG signal, and to manage the communication with the user interface.

Registered and processed data can be communicated to a PC or other data processing system, for example in accordance with the RS-232C or USB standard. This communication takes place via the gate 107.

The biofeedback circuit 108, which in this case is in the form of a stimulation influence, is controlled by the microprocessor 106, where it is possible to adjust/set the intensity of the current transmitted.

In a preferred embodiment of the apparatus, the stimulation signal is transmitted through the same multi-electrode as that which collects the muscle activity signal.

The circuit 109 shows a block diagram for a preferred embodiment for the processing of the EEG signal.

Signals which represent the activities which take place in the brain can be registered from the surface of the cranium. The electrical signal in the form of EEG is registered with the electrodes 104. Electrical activities recorded from the brain by the electrodes have a very low amplitude, max. $20\mu$-$200\mu$ Volt. The signals from the electrodes 104 are sent to the EEG signal processing part 105.

The information which is desired to be processed with the apparatus lies in the EEG signals, which are registered with the electrodes 104 in a frequency range between 0.5 and 80 Hz. The analogue signal processing part on EEG potentials takes place in 105, where the signal is processed so that the useful frequencies are amplified, filtered and rectified. The signals from the EEG electrodes 104 are sent to the microprocessor 106, where a processing of the EEG signal sampled by the analogue-to-digital converter is carried out. Data for the relevant parameters (frequency, amplitude, the RMS value), which are indicative of the sleep stage 2, are placed as reference in the microprocessor (106).

In an alternative embodiment of the apparatus, each of the signals from the right/left side of the jaw can be processed independently, and two independent stimulation signals can be sent out on each side of the jaw respectively, whereby it is achieved that bruxism which occurs only at the one side or the other side can be processed independently.

Figure 26:
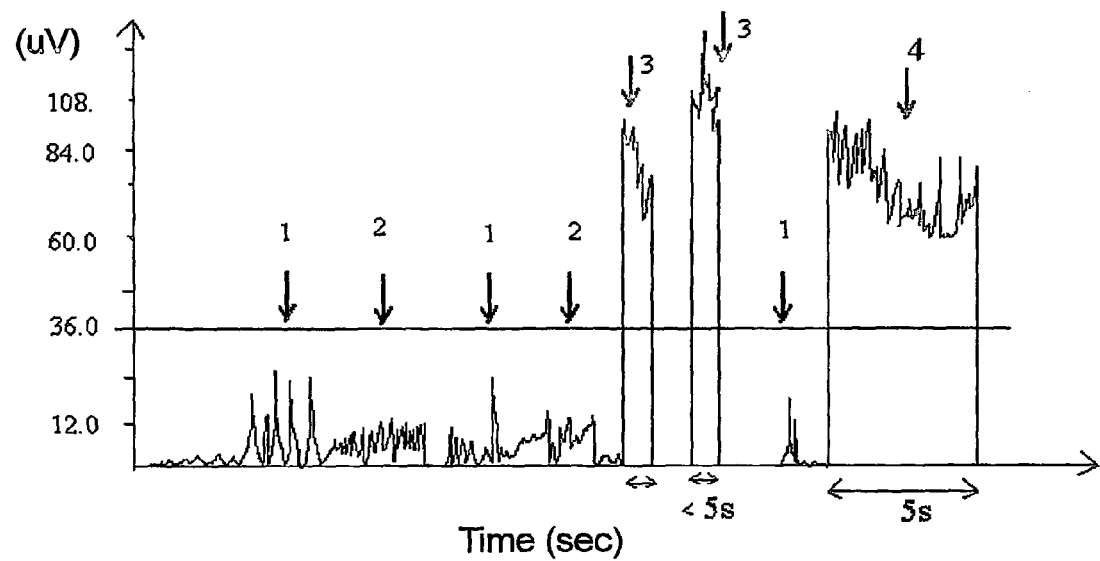
FIG. 26 shows a first signal which represents muscle activity as a function of time, where various forms of muscle activity occur.

FIG. 26 shows a first signal which represents muscle activity as a function of time, where various forms of muscle activity occur. The level for the threshold value Th mentioned earlier is indicated by a horizontal line at 36.0 microvolts. The signal comprises a number of characteristic signal sequences 1, 2, 3 and 4. The signal sequences 1 represent ordinary swallowing movements. The signal sequences 2 represent the muscle activity with speech and laughter. In these situations, no form of stimulation shall be triggered.

The signal sequences 3 represent ordinary teeth-clenching activity during sleep. This increased muscle activity will typically be related to dreaming by the patient. Despite the fact that the muscle activity exceeds the threshold value Th, no form of stimulation shall be triggered, as this muscle activity is not harmful to the teeth nor causes any pain due to the increased muscle activity. According to the invention, this decision can be made on the basis that the muscle activity only exceeds the threshold value for a limited interval of time, e.g. less than 5 seconds.

On the other hand, the signal sequence 4 represents biting activity during sleep which may be considered to be bruxism. This increased muscle activity has a somewhat longer duration than the signal sequences 3. It has been ascertained in practice that ordinary clenching and muscle activity can be distinguished from real bruxism by monitoring the activity level over a period of approx. 5 seconds, where the activity level exceeds the threshold value. If the activity level after this period still exceeds the threshold value, a stimulation signal is triggered so that the jaw muscle is relaxed and the bruxism is herewith terminated.

The period for which the activity level shall exceed the threshold value to bring about the triggering of a stimulation signal can be selected in an interval from approx. 2-4 seconds and up to 8-12 seconds, which can be done during the set-up procedure.

Figure 27:
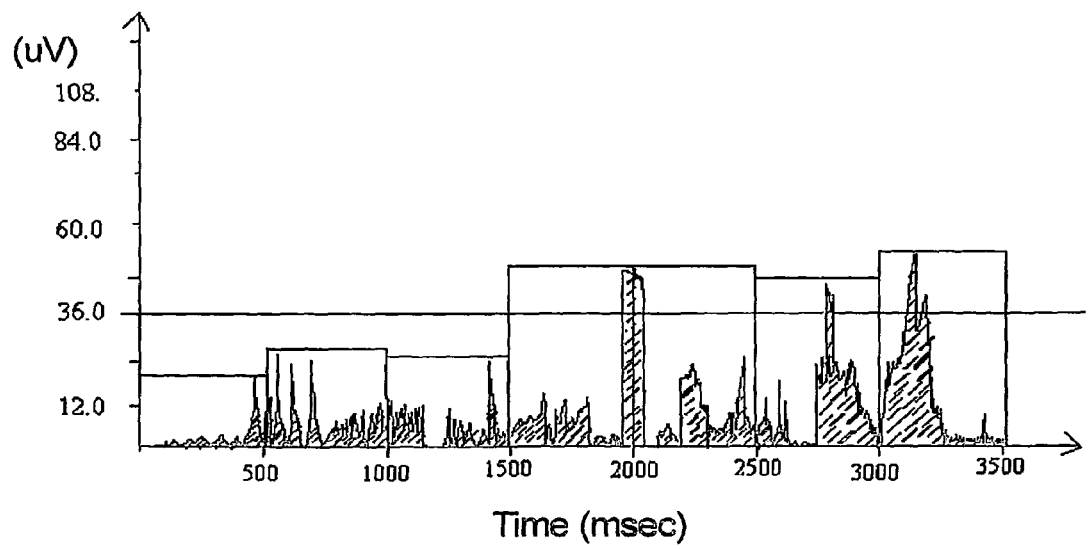
FIG. 27 shows a second signal which represents the muscle activity as a function of time, where an area and a RMS-value are calculated during each time interval (500 msec)

FIG. 27 shows a second signal which represents the muscle activity as a function of time. This shows how biopotential signals which are recorded from the masseter muscles are divided into windows with a time interval of, for example, 500 ms. During each time interval (500 ms), a calculation is made of the area below the curve and of the RMS value. These signals can be stored in memory for later analysis of the muscle activity.

Figure 28:
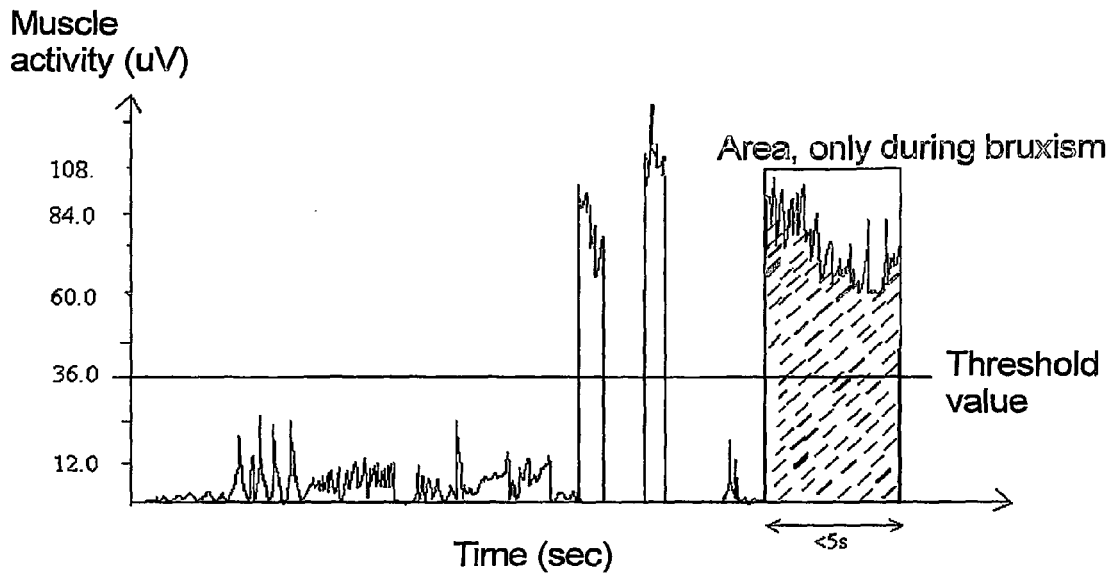
FIG. 28 shows a third signal, which represents muscle activity as a function of time, where an area and a RMS-value are calculated during muscle activities which lie above the threshold value and last longer than 5 seconds.

FIG. 28 shows a third signal which represents the muscle activity as a function of time. In a preferred embodiment, a calculation is made only of the area and RMS values for the sequences of the EMG signals which lie above the level of the threshold value and which, for example, last longer than 5 seconds.

Figure 29:
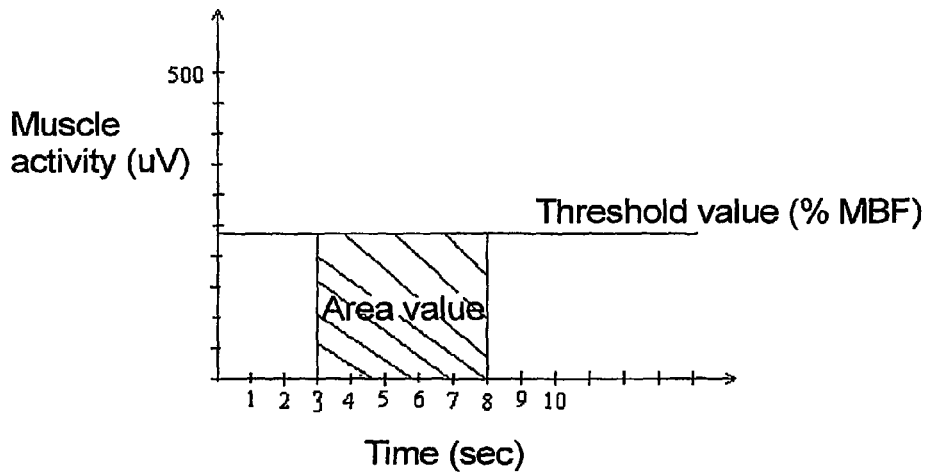
FIG. 29 shows the area below the Maximum Biting Force (MBF) in 5 seconds, which is used for determining the threshold value that may vary from 3 to 20% of MBF.

FIG. 29 shows the area below the maximum biting force, which is calculated in the microprocessor 121.

As discussed earlier in the description of the set-up process, a measurement must be made of the maximum biting force in the form of the EMG signals which are used to determine the threshold value, MBF (Maximum Biting Force). The threshold value typically lies in the region between 3 and 20% of the maximum force (MBF).

For the determination of the threshold value during the set-up procedure, the electrodes 101 and 104 must be mounted on the masseter muscles, and the user shall clench the teeth strongly together for 2-5 seconds. Thereafter, the apparatus must be adjusted to a certain % MBF, which can vary from 3 to 20% of MBF, corresponding to a desired threshold value.

On the basis of the threshold value found, the microcomputer 106 calculates an area value which determines when the stimulation shall be triggered. The area value is used as a form of reference and corresponds to that area which appears when the amplitude of an EMG signal has exceeded the threshold value for more than, for example, 5 seconds, such as keyed-in during the set-up procedure.

In order to stimulate the masseter muscles when the selected threshold value is exceeded, the potential on the output from the microcomputer must be converted to current. Since it cannot be known beforehand how much current shall be transmitted to the patient, so that a pain threshold is not exceeded, there must be a possibility of adjustment of the intensity of the current transmitted, which can be effected in several ways, as will be well-known by those skilled in the art.

Figure 30:
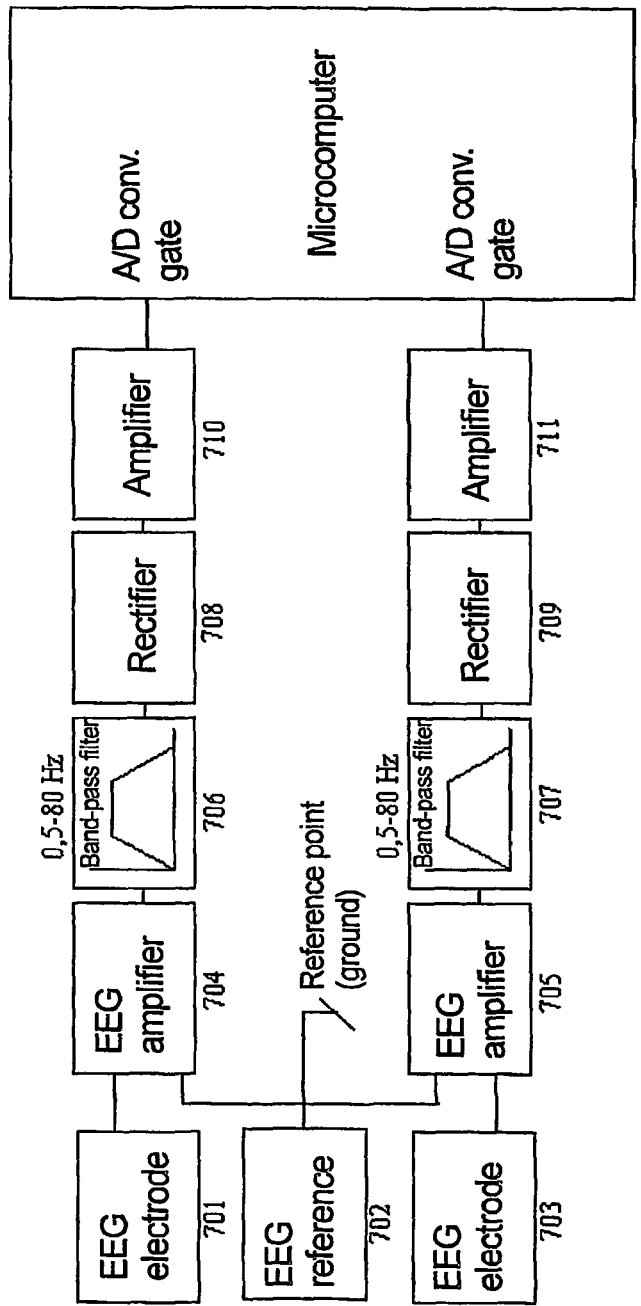
FIG. 30 shows the EEG-signal processing procedure, which is a method for analyzing the electric activities of a brain. These activities contribute primarily to potentials that may be measured on the surface of the scull.

FIG. 30 shows a block diagram for a preferred embodiment for the EEG signal processing. By means of EEG signal processing, it is possible to register/analyse the stages of sleep, which in professional language is called REM sleep (Rapid Eye Movement sleep). The sleep is divided into the stages REM 1-4, where REM1 is defined as that stage at which a person has just fallen asleep, and REM4 as the stage of deepest sleep.

As mentioned earlier, bruxism occurs mostly in sleep stage 2 and during awakening.

In the apparatus it is possible to analyse the EEG signals in combination with EMG-signal processing, so that the periods of bruxism can be analysed in various stages of sleep. Moreover, the apparatus can be set so that the stimulation is triggered only when the patient is in sleep stage 2.

Electric signals which represent the activities which occur in the brain can be registered from the surface of the cranium. The electric signals are registered with the EEG electrodes 701 and 703 (where 702 is used as reference). The electrodes are used for the measurement of electrical activities in the form of EEG signals, and they are placed on the forehead over the eye.

The signals from the electrodes 701 and 703 are sent to respective EEG amplifiers 704 and 705. The amplifiers 704 and 705 are instrumentation amplifiers which have very high input impedance and are good at suppressing so-called common-mode voltages. The amplified signals from the amplifiers 704 and 705 are filtered by means of the band-pass filters 706 and 707, herewith increasing the signals' signal/noise ratio. The information which is desired to be processed by the apparatus lies in the EEG signals, which are registered with the electrodes 701 and 703 in a frequency range between 0.5 and 80 Hz. The band-pass filters 706 and 707 therefore have lower and upper −3 dB limit frequencies of 0.5 Hz and 80 Hz respectively. The stop band herewith comprises frequencies lower than 0.5 Hz and frequencies higher than 80 Hz. The signals from the band-pass filters 706 and 707 are rectified by means of the rectification circuit 708 and 709, so that the voltage span from a unipolar voltage (±) is converted to a positive voltage.

The signals from the rectification circuit 708 and 709 are amplified in the amplification circuit 710 and 711, so that the microprocessor 106 and a built-in analogue-to-digital converter can be utilised to the best possible extent.

The signals from the EEG electrodes 701 and 703 are sent to the microprocessor 106, where a processing takes place of the EEG signal sampled by the analogue-to-digital converter. Data for the relevant parameters (frequency, amplitude, RMS value), which are indicative for sleep stage 2), are placed as a programme in the microcomputer 106.

When the user falls asleep, the sleep stages will be scanned, for example every 1 second, and the EEG signals are continuously compared with the parameters which correspond to the brain activities which occur in sleep stage 2. These signals are of different amplitudes and frequency, depending on the sleep stages 1-4, and in this manner the microcomputer can recognise the signal/frequency of the relevant sleep stage (in this case sleep stage 2).

For the determination of the sleep stages, use will typically be made of 2 concepts, namely amplitude of EEG signals and frequency of EEG signals.

In the apparatus there is the possibility of analysing the EEG signals (a method for the analysis of the brain's electrical activities and registration of the sleep stages) in combination with EMG signal processing, so that the periods of bruxism can be analysed in different stages of sleep.

In the stages of lighter sleep a general increase in the muscle activity can be observed in relation to the deeper sleep. Bruxism thus occurs mainly in sleep stage 2 and during awakening. But in the stages of deeper sleep there can occur some ordinary teeth-clenching activity, which with an EMG registration alone can be difficult to distinguish from bruxism. When this is combined with a system for the determination of the sleep stages, the certainty in the detection of nightly bruxism will be far greater.

Therefore, the patient must use the apparatus for a minimum of 7 nights without activation of the feedback (the set-up period), where signals/frequencies from both EMG and EEG measurements are stored in a memory. Thereafter, an analysis is made of the correlation between EEG (sleep stages) and EMG (teeth clenching activity in the masseter or temporalis muscles), where the result will be used for the detection of bruxism and herewith activation of the feedback. In this way the apparatus is able to be adjusted individually.

In the microprocessor, continuous analysis is made of signals from both the EMG and EEG electrodes, for example every half a second. These values are compared periodically with the reference values, for example in the form of an individual table which is defined during the set-up period, and when there is agreement between these values, the microprocessor will indicate with great certainty that the user is grinding his/her teeth. In this manner the certainty is greatly increased with regard to the triggering of stimulation, so that the normal teeth-clenching activity or a sudden spike which exceeds the threshold value will not give rise to a triggering of the feedback (the stimulation).

When this method is used for the detection of bruxism, the processing of the EMG signal will be able to be digitalised to a greater degree.

The patient shall merely go through the set-up period, which as mentioned as an example can extend over 7 nights or another suitable period.

Figure 31:
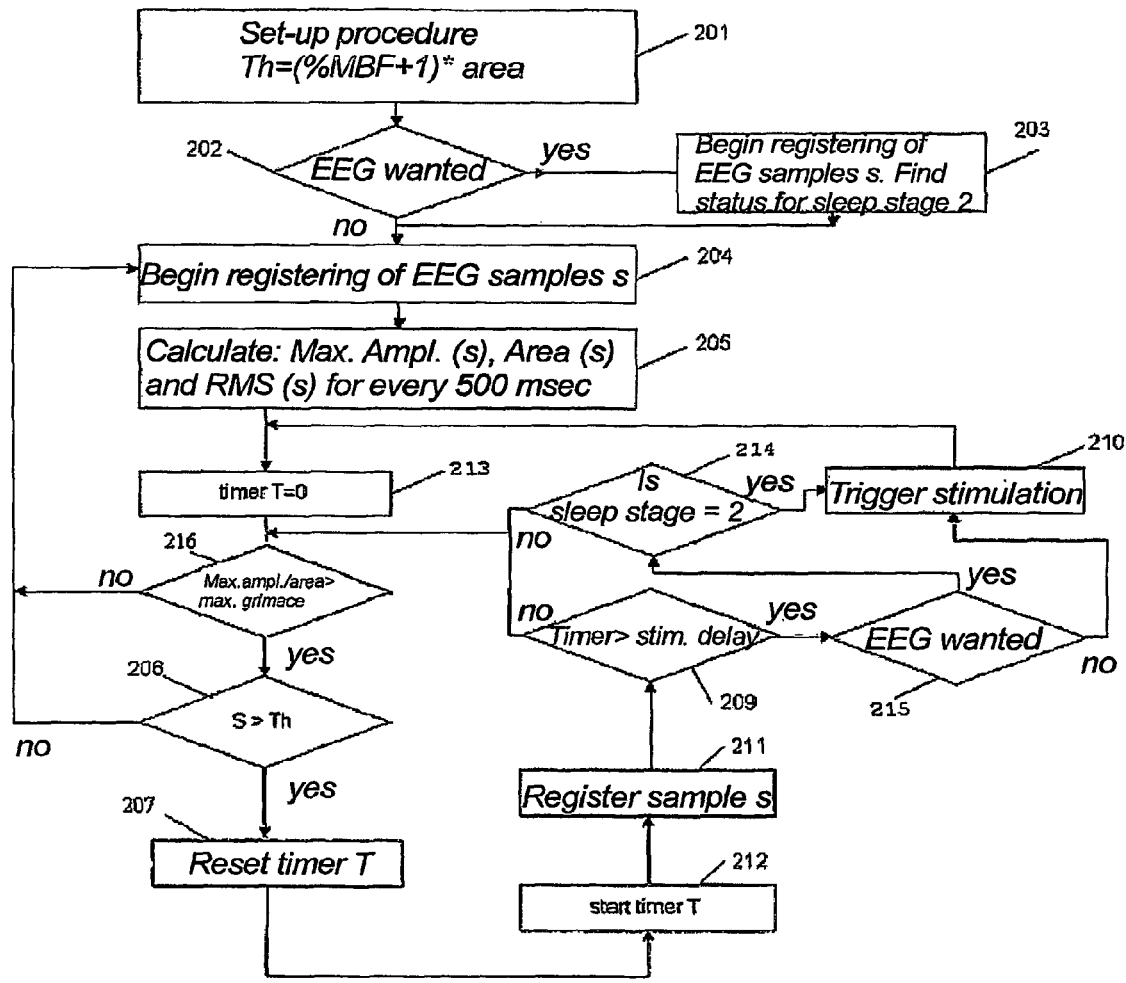
FIG. 31 shows a route diagram for the measuring of muscle activity and triggering of a stimulation signal.

FIG. 31 shows a routing diagram for the measurement of the muscle activity and triggering of a stimulation signal. This routing diagram can be implemented as a programme for the microprocessor 106.

In the first stage 201 in the routing diagram, the patient must go through the set-up procedure (as described in connection with e.g. FIG. 3) in order to register the personal parameters in the form of MBF (maximum biting force), amplitude of the grimaces, stimulation delay/duration and threshold value (Th) in the apparatus. The area below the signal is calculated and, on the basis of the percentage, a threshold value Th will be calculated in the microprocessor 106 for the level of muscle activity which is required to trigger a stimulation.

Alternatively, this threshold value can be calculated automatically based on measurements of the muscle activity, or retrieved from a memory in which the threshold value has been stored earlier.

In stage 202 it is defined whether an analysis of the sleep stages is to be carried out in combination with the EMG signal processing.

In stage 203 it is presupposed that the earlier-mentioned EEG electrodes 104 are mounted on the surface of the patient's cranium, and information (frequency and amplitude) can thus be registered concerning the sleep stages in the form of sample S.

In stage 204 it is presupposed that the earlier-mentioned electrodes 101 are mounted on the jaw of a patient, and information concerning the muscle activity can thus be registered in the form of samples S. The muscle activity is registered in 205, where calculations are made of the area, max. amplitude and RMS value for a time interval of, for example, 500 ms. After stage 205 there follows a loop in the routing diagram.

In stage 213 the timer T is set/reset to zero. In stage 216 it is decided whether the amplitude/the area of registered samples S exceeds the max. value of the grimaces (determined during the set-up procedure). If the threshold value is exceeded, it is decided whether the amplitude/the area of registered samples S exceeds the threshold value Th in 206. If the threshold value is exceeded, the timer is set to zero in stage 207 or new samples are merely registered in stage 204. The timer T in stage 212 is started and new samples S are registered in stage 211.

In stage 209 it is decided whether the muscle activity in the form of the amplitude/area of registered samples has exceeded the threshold value Th more than the stimulation delay (determined during the set-up procedure).

In stage 215 it is examined whether analysis of the sleep stages has been desired or not. If this is the case, the EEG signals will be continuously compared with the parameters for sleep stage 2 in stage 214. Data for the relevant parameters (frequency, amplitude) which are indicative for sleep stage 2 are placed as a programme in the microprocessor 106.

If an analysis of the sleep stages is desired (EEG), the stimulation will not be triggered until the amplitude of the EMG signals has exceeded the threshold value by more than the stimulation delay at the same time that the patient is in sleep stage 2.

In stage 210 a stimulation is triggered in the form of a stimulation signal which is applied to the patient's jaw through one or both of the earlier-mentioned electrodes. Alternatively, if less time has elapsed than the stimulation delay while the threshold value has been exceeded, no stimulation signal is triggered. It is hereby achieved that no stimulation signal is triggered before it has been verified that there is a situation in which real bruxism is present. In this way, ill-timed stimulations of the jaw muscles are avoided.

The shown routing diagram can be implemented so that two independent signal paths, one for each side of the jaw, can be processed independently.

Figure 32:
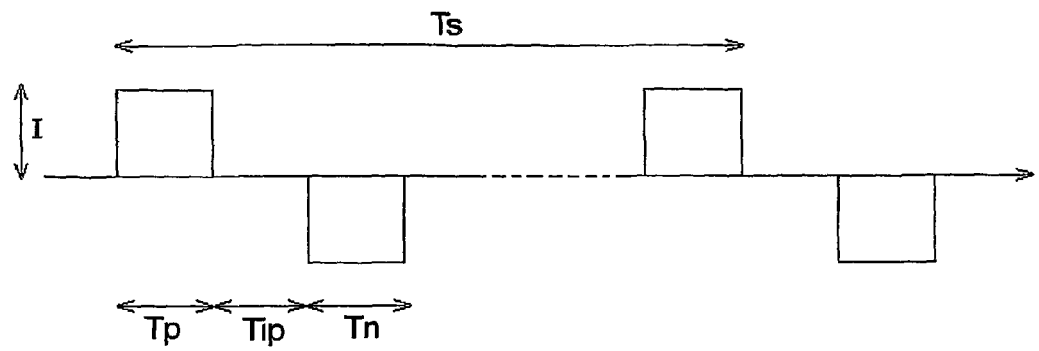
FIG. 32 shows an example of a stimulation signal.

FIG. 32 shows an example of a stimulation signal. The stimulation signal consists of a pulse train where a positive pulse is followed by an interval of time until a negative pulse arrives. The shape of the stimulation signal is generated by the microprocessor 106. The parameters which describe the signal comprise the pulse length of the positive and the negative pulses Tp and Tn respectively, the interval of time between the two pulses, Tip, the repetition frequency, 1/Ts, and the amplitude I of the pulses.

In a preferred embodiment, the strength of the current or the amplitude I of the pulses is varied during a processing. Before processing commences, a minimum and a maximum amplitude for the stimulation signal is specified. When and if bruxism is detected, i.e. the threshold value Th is exceeded for more than the stimulation delay, a stimulation signal shall be triggered. The stimulation signal has a minimum amplitude as start value. If this minimum amplitude is sufficient to terminate the bruxism state, the amplitude of the stimulation signal is held at this level. Alternatively, if the minimum amplitude is not sufficient to terminate the bruxism state, the amplitude is gradually increased at a certain rate until the bruxism state can be terminated by stimulation of the jaw muscle. However, the amplitude is not increased above the specified maximum amplitude.

The rate at which the amplitude is allowed to be increased is also called a "slew-rate". It is also possible to specify maximum and minimum values for this "slew-rate". By ramping the amplitude of the stimulation signal up or down in this manner, it is achieved that use is made of that intensity which is precisely sufficient to terminate the bruxism state. This is expedient since that stimulation amplitude which is necessary varies from patient to patient, just as that stimulation amplitude which is necessary can vary over time for the same patient.

Moreover, controlled by an analogue switch from the microprocessor, use can be made of so-called multi-electrodes which can be used both for the stimulation of a muscle as well to register the muscle's activity.

Figure 33:
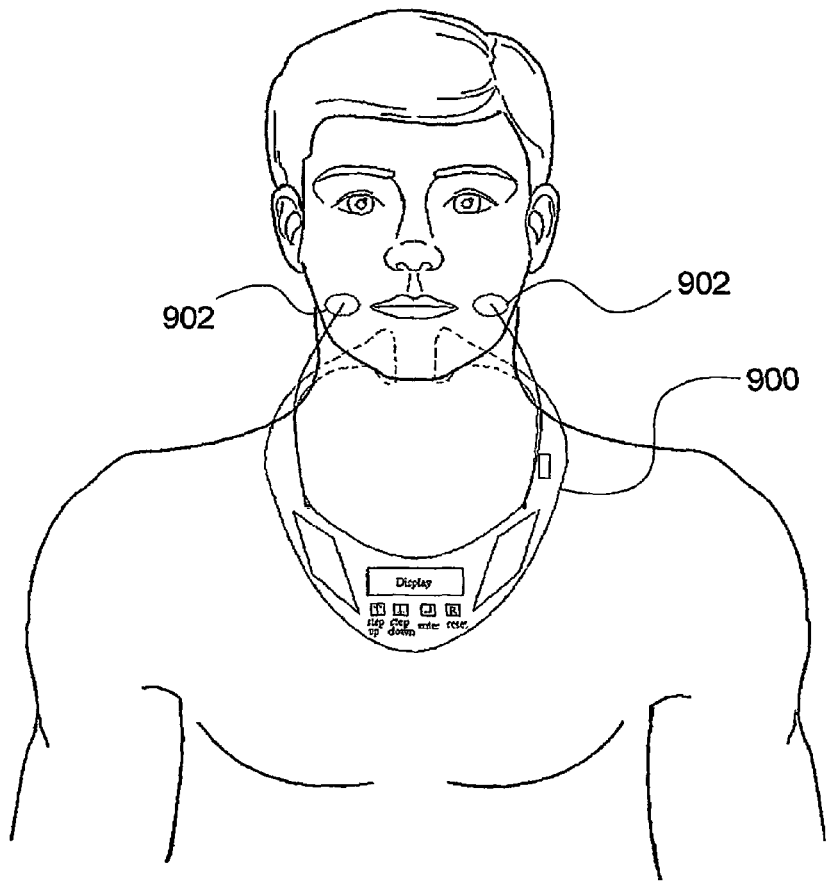
FIGS. 33 and 34 show an embodiment of an Anti-Bruxism Module, where this embodiment of the apparatus is placed around the neck, and where EMG electrodes can be mounted on the jaw muscles and/or the forehead (above the eyes).

In FIG. 33 is shown an embodiment of an Anti-Bruxism Module 900, where this embodiment of the apparatus shall be placed around the neck, and where the EMG electrodes 902 can be mounted on the jaw muscles and/or on the forehead (above the eyes). Furthermore, there can be the possibility of the connection of EEG electrodes is this is desired.

Figure 34:
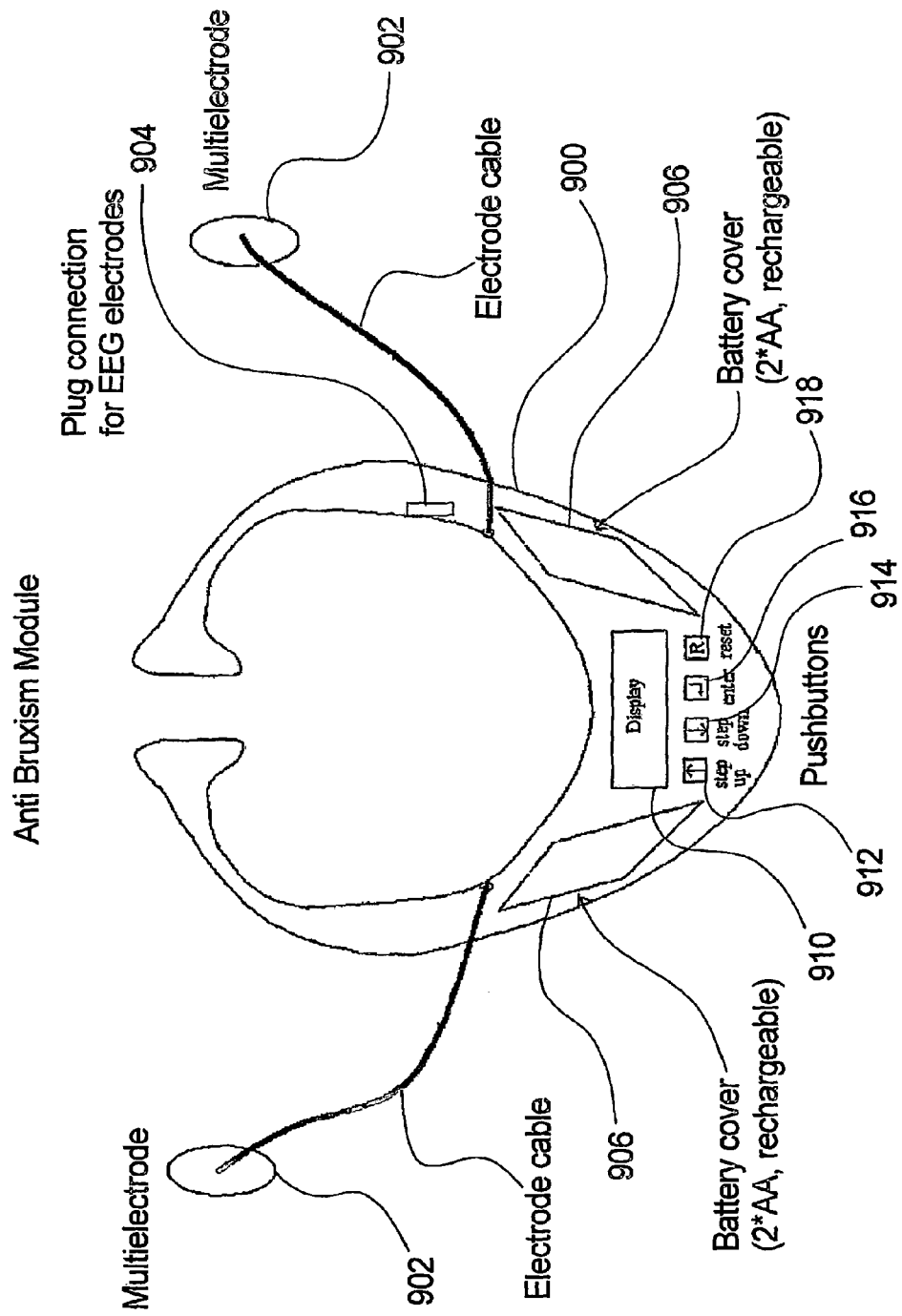

FIG. 34 shows an enlarged illustration of a corresponding module 900, where plug connections 904 for EEG electrodes are illustrated. As will be seen, the EMG electrodes 902 are configured as multi-electrodes, and the figure also shows that the module comprises batteries in battery compartments 906 for operation of the signal recording, digitalisation, transmission and operation during set-up procedures etc. It is also shown that the module has a display 910 and pushbuttons or the like 912-918 for use in the keying-in during the set-up procedure, for example in the selection of the level of stimuli, for keying-in the desired threshold level etc.

In the above, the invention has been explained in detail with reference to specific embodiments and as illustrated in the drawings. As it will obvious to the skilled person, the invention may be performed in many other forms and variations and should not be limited to the examples of the invention illustrated above. The scope of the invention will be defined by the claims.

The invention claimed is:

1. An apparatus for detecting bruxism and providing feedback to a user, said apparatus comprising:
   a sensor system operable to measure the muscular activity of a user's jaw associated with a level of biting force and generate a signal corresponding thereto;
   a signal processor which is in communication with said sensor system and is operable to receive said signal as a function of time, wherein said signal processor is configured such that the signal received from the sensor system as a function of time is divided into windows of a predefined time interval and configured such that a calculation of the area under the curve of the muscular activity vs. time is provided for each time window to yield the total biting power for each time window and calculate a level of muscular activity and integrate said level vs. time, so as to provide a processed signal, and
   a feedback signal generator which is in communication with said signal processor, said feedback signal generator being operable to receive said processed signal from said sensor system and generate a feedback signal, and direct said feedback signal to said user if the level of muscular activity measured by said sensor system exceeds a predefined threshold level of muscular activity for a predefined period of time.

2. The apparatus of claim 1, wherein said feedback signal is provided on the basis of an evaluation comprising an area calculation.

3. The apparatus of claim 1, wherein said apparatus is configured such that said total biting power of each time window is stored.

4. The apparatus of claim 1, wherein said sensor system comprises one or more electrodes for sensing of EMG-signals.

5. The apparatus of claim 1, wherein said signal processor is operable to calculate a threshold level of muscular activity which is in the range of 3-20% of a level of muscular activity which is associated with a maximum level of biting force.

6. The apparatus claim 1, wherein said feedback signal generator includes a control system for controlling the duration and/or intensity of said feedback signal.

7. The apparatus of claim 1, wherein said sensor system is operable to detect EMG signals.

8. The apparatus of claim 1, wherein said apparatus is operable to store data derived from said sensor system and/or said signal processor and/or said feedback signal generator.

9. The apparatus of claim 8, further including a computer and a system for transferring said stored data thereto.

10. The apparatus of claim 1, further comprising a user module configured to be worn on a user's head.

11. The apparatus of claim 1, further comprising a display device operable to display information and/or results derived from said sensor system and/or said signal processor and/or said threshold signal generator.

12. The apparatus of claim 1, wherein said apparatus is operable to store said threshold level of muscular activity in an associated, non-transitory memory.

13. The apparatus of claim 1, wherein said signal processor is operable to accumulate data and determine and store frequency patterns corresponding to muscular activity and relating to bruxism.

14. The apparatus of claim 1, wherein said apparatus is configured to be individually adaptable by having adjustment means for adjusting the level of said feedback signal.

* * * * *